United States Patent
Benson et al.

(10) Patent No.: US 12,318,144 B2
(45) Date of Patent: Jun. 3, 2025

(54) SYSTEMS AND METHODS FOR PLANNING A PATIENT-SPECIFIC SPINAL CORRECTION

(71) Applicant: Medicrea International SA, Rillieux-la-Pape (FR)

(72) Inventors: Nicholas Benson, Collierville, TN (US); Thomas Mosnier, Rochetaillee sur Saone (FR)

(73) Assignee: MEDICREA INTERNATIONAL SA (FR)

( * ) Notice: Subject to any disclaimer, the term of this patent is extended or adjusted under 35 U.S.C. 154(b) by 986 days.

(21) Appl. No.: 17/355,392

(22) Filed: Jun. 23, 2021

(65) Prior Publication Data

US 2022/0409279 A1    Dec. 29, 2022

(51) Int. Cl.
   *A61B 34/10*      (2016.01)
   *A61B 17/70*      (2006.01)
   (Continued)

(52) U.S. Cl.
   CPC .......... *A61B 34/10* (2016.02); *A61B 17/7086* (2013.01); *A61B 90/36* (2016.02);
   (Continued)

(58) Field of Classification Search
   CPC ................ A61B 2090/367; G06T 2207/30052
   See application file for complete search history.

(56) References Cited

U.S. PATENT DOCUMENTS

| | | |
|---|---|---|
| 4,382,438 A | 5/1983 | Jacobs |
| 5,006,984 A | 4/1991 | Steele |
| (Continued) | | |

FOREIGN PATENT DOCUMENTS

| | | |
|---|---|---|
| WO | 2017064719 A1 | 4/2017 |
| WO | 2018131045 A1 | 7/2018 |
| (Continued) | | |

OTHER PUBLICATIONS

International Search Report in Application No. PCT/IB2022/000331 mailed Nov. 25, 2022.
(Continued)

*Primary Examiner* — Patricia J Park
(74) *Attorney, Agent, or Firm* — FOX ROTHSCHILD LLP

(57) ABSTRACT

Systems and methods are provided to plan a spinal correction surgery. The method includes measuring parameters of a spine in a two-dimensional (2D) spinal image including a thoracic Cobb angle and a thoracic kyphosis (TK) and transforming the 2D image to a three-dimensional (3D), spinal image representation. The transforming includes performing segmentation of spine elements in the 2D image, and applying a formula based on the thoracic Cobb angle and the TK to the spine elements. The method includes identifying a TK goal having a post-operative TK value to selected spine elements, transforming a gap of the spine elements representative of a difference between the pre-operative TK in 3D spinal image representation and the TK goal to create a 3D post-operative spinal image representation, and determining a first rod design based on the 3D post-operative spinal image representation to achieve the post-operative TK value in the spine elements.

21 Claims, 13 Drawing Sheets

(51) Int. Cl.
*A61B 90/00* (2016.01)
*G06T 7/10* (2017.01)

(52) U.S. Cl.
CPC .......... *G06T 7/10* (2017.01); *A61B 2034/104* (2016.02); *A61B 2034/105* (2016.02); *A61B 2034/108* (2016.02); *A61B 2090/367* (2016.02); *G06T 2207/10028* (2013.01); *G06T 2207/30012* (2013.01); *G06T 2207/30052* (2013.01)

(56) References Cited

U.S. PATENT DOCUMENTS

| | | | |
|---|---|---|---|
| 5,163,440 A | 11/1992 | DeLuca et al. | |
| 5,209,752 A | 5/1993 | Ashman et al. | |
| 5,224,035 A | 6/1993 | Yamashita et al. | |
| 5,251,127 A | 10/1993 | Raab | |
| 5,291,901 A | 3/1994 | Graf | |
| 5,305,203 A | 4/1994 | Raab | |
| 5,312,405 A | 5/1994 | Korotko et al. | |
| 5,413,116 A | 5/1995 | Radke et al. | |
| 5,514,180 A | 5/1996 | Heggeness et al. | |
| 5,667,506 A | 9/1997 | Sutterlin | |
| 5,748,767 A | 5/1998 | Raab | |
| 5,785,663 A | 7/1998 | Sarvazyan | |
| 6,015,409 A | 1/2000 | Jackson | |
| 6,213,958 B1 | 4/2001 | Winder | |
| 6,282,437 B1 | 8/2001 | Franck et al. | |
| 6,302,888 B1 | 10/2001 | Mellinger et al. | |
| 6,364,849 B1 | 4/2002 | Wilcox | |
| 6,385,475 B1 | 5/2002 | Cinquin et al. | |
| 6,409,684 B1 | 6/2002 | Wilk | |
| 6,443,953 B1 | 9/2002 | Perra et al. | |
| 6,499,488 B1 | 12/2002 | Hunter et al. | |
| 6,565,519 B2 | 5/2003 | Benesh | |
| 6,585,666 B2 | 7/2003 | Suh et al. | |
| 6,711,432 B1 | 3/2004 | Krause et al. | |
| 6,715,213 B2 | 4/2004 | Richter | |
| 6,716,213 B2 | 4/2004 | Shitoto | |
| 6,746,449 B2 | 6/2004 | Jones et al. | |
| 6,786,930 B2 | 9/2004 | Biscup | |
| 7,066,938 B2 | 6/2006 | Slivka et al. | |
| 7,338,526 B2 | 3/2008 | Steinberg | |
| 7,509,183 B2 | 3/2009 | Lin et al. | |
| 7,534,263 B2 | 5/2009 | Burdulis, Jr. et al. | |
| 7,542,791 B2 | 6/2009 | Mire et al. | |
| 7,570,791 B2 | 8/2009 | Frank et al. | |
| 7,606,613 B2 | 10/2009 | Simon et al. | |
| 7,611,522 B2 | 11/2009 | Gorek | |
| 7,618,451 B2 | 11/2009 | Berez et al. | |
| 7,634,119 B2 | 12/2009 | Tsougarakis et al. | |
| 7,635,367 B2 | 12/2009 | Groiso | |
| 7,639,866 B2 | 12/2009 | Pomero et al. | |
| 7,660,623 B2 | 2/2010 | Hunter et al. | |
| 7,674,293 B2 | 3/2010 | Kuiper et al. | |
| 7,715,602 B2 | 5/2010 | Richard | |
| 7,763,054 B2 | 7/2010 | Clement et al. | |
| 7,824,413 B2 | 11/2010 | Varieur et al. | |
| 7,835,778 B2 | 11/2010 | Foley et al. | |
| 7,840,253 B2 | 11/2010 | Tremblay et al. | |
| 7,862,593 B2 | 1/2011 | Clement et al. | |
| 7,918,887 B2 | 4/2011 | Roche | |
| 7,953,471 B2 | 5/2011 | Clayton et al. | |
| 7,974,677 B2 | 7/2011 | Mire et al. | |
| 7,981,158 B2 | 7/2011 | Fitz et al. | |
| 7,996,061 B2 | 8/2011 | Mollard et al. | |
| 7,996,064 B2 | 8/2011 | Simon et al. | |
| 8,000,926 B2 | 8/2011 | Roche et al. | |
| 8,036,441 B2 | 10/2011 | Frank et al. | |
| 8,038,716 B2 | 10/2011 | Duggal et al. | |
| 8,046,050 B2 | 10/2011 | Govari et al. | |
| 8,066,708 B2 | 11/2011 | Lang et al. | |
| 8,077,950 B2 | 12/2011 | Tsougarakis et al. | |
| 8,083,778 B2 | 12/2011 | Clement et al. | |
| 8,105,330 B2 | 1/2012 | Fitz et al. | |
| 8,142,842 B2 | 3/2012 | Sugita et al. | |
| 8,196,825 B2 | 6/2012 | Turner et al. | |
| 8,211,109 B2 | 7/2012 | Groiso | |
| 8,211,153 B2 | 7/2012 | Shaolian et al. | |
| 8,234,097 B2 | 7/2012 | Steines et al. | |
| 8,241,296 B2 | 8/2012 | Wasielewski | |
| 8,246,680 B2 | 8/2012 | Betz et al. | |
| 8,265,790 B2 | 9/2012 | Amiot et al. | |
| 8,270,253 B1 | 9/2012 | Roche et al. | |
| 8,275,594 B2 | 9/2012 | Lin et al. | |
| 8,308,772 B2 | 11/2012 | Clement et al. | |
| 8,308,775 B2 | 11/2012 | Clement et al. | |
| 8,337,501 B2 | 12/2012 | Fitz et al. | |
| 8,357,111 B2 | 1/2013 | Caillouette et al. | |
| 8,357,166 B2 | 1/2013 | Aram et al. | |
| 8,372,075 B2 | 2/2013 | Groiso | |
| 8,377,073 B2 | 2/2013 | Wasielewski | |
| 8,394,142 B2 | 3/2013 | Bertagnoli et al. | |
| 8,398,681 B2 | 3/2013 | Augostino et al. | |
| 8,400,312 B2 | 3/2013 | Hotokebuchi et al. | |
| 8,414,592 B2 | 4/2013 | Quimno | |
| 8,442,621 B2 | 5/2013 | Gorek et al. | |
| 8,457,930 B2 | 6/2013 | Schroeder | |
| 8,465,527 B2 | 6/2013 | Clement | |
| 8,494,805 B2 | 7/2013 | Roche et al. | |
| 8,506,632 B2 | 8/2013 | Ganem et al. | |
| 8,532,806 B1 | 9/2013 | Masson | |
| 8,535,337 B2 | 9/2013 | Chang et al. | |
| 8,549,888 B2 | 10/2013 | Isaacs | |
| 8,556,983 B2 | 10/2013 | Bojarski et al. | |
| 8,588,892 B2 | 11/2013 | Hladio et al. | |
| 8,636,776 B2 | 1/2014 | Rosenberg et al. | |
| 8,672,948 B2 | 3/2014 | Lemaitre | |
| 8,685,093 B2 | 4/2014 | Anderson et al. | |
| 8,690,888 B2 | 4/2014 | Stein et al. | |
| 8,705,829 B2 | 4/2014 | Frank et al. | |
| 8,718,820 B2 | 5/2014 | Amiot et al. | |
| 8,758,357 B2 | 6/2014 | Frey | |
| 8,775,133 B2 | 7/2014 | Schroeder | |
| 8,777,877 B2 | 7/2014 | Stein et al. | |
| 8,784,339 B2 | 7/2014 | Stein et al. | |
| 8,801,786 B2 | 8/2014 | Bernard et al. | |
| 8,814,877 B2 | 8/2014 | Wasielewski | |
| 8,814,915 B2 | 8/2014 | Hess et al. | |
| 8,852,237 B2 | 10/2014 | Kalfas et al. | |
| 8,855,389 B1 | 10/2014 | Hoffmann et al. | |
| 8,864,764 B2 | 10/2014 | Groiso | |
| 8,870,889 B2 | 10/2014 | Frey | |
| 8,900,316 B2 | 12/2014 | Lenz et al. | |
| 8,911,448 B2 | 12/2014 | Stein | |
| 8,926,673 B2 | 1/2015 | Clement et al. | |
| 8,945,133 B2 | 2/2015 | Stein et al. | |
| 8,956,416 B2 | 2/2015 | McCarthy | |
| 8,974,467 B2 | 3/2015 | Stone | |
| 8,983,813 B2 | 3/2015 | Miles et al. | |
| 8,998,962 B2 | 4/2015 | Birch | |
| 9,011,448 B2 | 4/2015 | Roche et al. | |
| 9,034,037 B2 | 5/2015 | Fiere et al. | |
| 9,039,772 B2 | 5/2015 | Park et al. | |
| 9,056,017 B2 | 6/2015 | Kotlus | |
| 9,066,701 B1 | 6/2015 | Finley et al. | |
| 9,066,734 B2 | 6/2015 | Schoenefeld et al. | |
| 9,078,755 B2 | 7/2015 | Mahfouz | |
| 9,101,492 B2 | 8/2015 | Mangione et al. | |
| 9,115,998 B2 | 8/2015 | Proulx et al. | |
| 9,119,572 B2 | 9/2015 | Gorek et al. | |
| 9,119,671 B2 | 9/2015 | Kast | |
| 9,125,680 B2 | 9/2015 | Kostrzewski et al. | |
| 9,144,440 B2 | 9/2015 | Aminian | |
| 9,144,470 B2 | 9/2015 | Proulx et al. | |
| 9,168,153 B2 | 10/2015 | Bettenga | |
| 9,173,661 B2 | 11/2015 | Metzger et al. | |
| 9,180,015 B2 | 11/2015 | Fitz et al. | |
| 9,192,412 B2 | 11/2015 | Meyrat et al. | |
| 9,198,678 B2 | 12/2015 | Frey et al. | |
| 9,232,955 B2 | 1/2016 | Bonin, Jr. et al. | |
| 9,233,001 B2 | 1/2016 | Miles et al. | |
| 9,237,952 B2 | 1/2016 | Kurtz | |
| 9,248,023 B2 | 2/2016 | Ries et al. | |

(56) References Cited

U.S. PATENT DOCUMENTS

| | | |
|---|---|---|
| 9,250,620 B2 | 2/2016 | Kotlus |
| 9,278,010 B2 | 3/2016 | Gibson et al. |
| 9,283,048 B2 | 3/2016 | Kostrzewski et al. |
| 9,289,221 B2 | 3/2016 | Gelaude et al. |
| 9,289,270 B2 | 3/2016 | Gielen et al. |
| 9,295,482 B2 | 3/2016 | Fitz et al. |
| 9,295,497 B2 | 3/2016 | Schoenefeld et al. |
| 9,295,561 B2 | 3/2016 | Ball et al. |
| 9,301,768 B2 | 4/2016 | Buza et al. |
| 9,308,050 B2 | 4/2016 | Kostrzewski et al. |
| 9,308,091 B2 | 4/2016 | Lang |
| 9,314,275 B2 | 4/2016 | Clement et al. |
| 9,314,343 B2 | 4/2016 | Parisi et al. |
| 9,320,547 B2 | 4/2016 | Augostino |
| 9,320,604 B2 | 4/2016 | Miles et al. |
| 9,326,780 B2 | 5/2016 | Wong et al. |
| 9,339,277 B2 | 5/2016 | Jansen et al. |
| 9,345,492 B2 | 5/2016 | Stein et al. |
| 9,358,051 B2 | 6/2016 | Sournac et al. |
| 9,358,130 B2 | 6/2016 | Livorsi et al. |
| 9,358,136 B2 | 6/2016 | Stein et al. |
| 9,364,370 B2 | 6/2016 | Kuhnel |
| 9,381,085 B2 | 7/2016 | Axelson, Jr. et al. |
| 9,387,015 B2 | 7/2016 | Taylor |
| 9,392,953 B1 | 7/2016 | Gharib |
| 9,393,052 B2 | 7/2016 | Berg et al. |
| 9,398,962 B2 | 7/2016 | Steinberg |
| 9,402,726 B2 | 8/2016 | Linderman et al. |
| 9,408,615 B2 | 8/2016 | Fitz et al. |
| 9,408,642 B2 | 8/2016 | Wong et al. |
| 9,408,698 B2 | 8/2016 | Miles et al. |
| 9,414,940 B2 | 8/2016 | Stein et al. |
| 9,433,443 B2 | 9/2016 | Montello et al. |
| 9,439,659 B2 | 9/2016 | Schoenefeld et al. |
| 9,439,767 B2 | 9/2016 | Bojarski et al. |
| 9,439,781 B2 | 9/2016 | Gibson |
| 9,445,913 B2 | 9/2016 | Donner et al. |
| 9,452,022 B2 | 9/2016 | McIntosh et al. |
| 9,452,023 B2 | 9/2016 | Boillot et al. |
| 9,452,050 B2 | 9/2016 | Miles et al. |
| 9,452,064 B2 | 9/2016 | Trautwein et al. |
| 9,468,436 B2 | 10/2016 | Groiso |
| 9,468,502 B2 | 10/2016 | Wiebe, III et al. |
| 9,491,415 B2 | 11/2016 | Deitz et al. |
| 9,492,183 B2 | 11/2016 | Wilkinson et al. |
| 9,495,483 B2 | 11/2016 | Steines et al. |
| 9,495,509 B2 | 11/2016 | Amiot et al. |
| 9,498,260 B2 | 11/2016 | Funk et al. |
| 9,504,502 B2 | 11/2016 | Kuiper et al. |
| 9,510,771 B1 | 12/2016 | Finley et al. |
| 9,510,864 B2 | 12/2016 | Devito |
| 9,517,134 B2 | 12/2016 | Lang |
| 9,517,143 B2 | 12/2016 | Prevost et al. |
| 9,526,514 B2 | 12/2016 | Kelley et al. |
| 9,532,730 B2 | 1/2017 | Wasielewski |
| 9,539,031 B2 | 1/2017 | Fauth |
| 9,539,116 B2 | 1/2017 | Claypool et al. |
| 9,539,760 B2 | 1/2017 | Stahl et al. |
| 9,547,897 B2 | 1/2017 | Parent et al. |
| 9,549,782 B2 | 1/2017 | Park et al. |
| 9,554,411 B1 | 1/2017 | Hall et al. |
| 9,554,910 B2 | 1/2017 | Vanasse et al. |
| 9,561,115 B2 | 2/2017 | Elahinia et al. |
| 9,566,075 B2 | 2/2017 | Carroll et al. |
| 9,579,043 B2 | 2/2017 | Chien et al. |
| 9,585,597 B2 | 3/2017 | McCaulley et al. |
| 9,597,096 B2 | 3/2017 | Aghazadeh |
| 9,597,156 B2 | 3/2017 | Amiot et al. |
| 9,603,613 B2 | 3/2017 | Schoenefeld et al. |
| 9,603,623 B2 | 3/2017 | Brooks et al. |
| 9,603,711 B2 | 3/2017 | Bojarski et al. |
| 9,610,086 B2 | 4/2017 | Park et al. |
| 9,615,834 B2 | 4/2017 | Agnihotri et al. |
| 9,622,712 B2 | 4/2017 | Munro et al. |
| 9,629,723 B2 | 4/2017 | Parisi et al. |
| 9,636,181 B2 | 5/2017 | Isaacs |
| 9,642,633 B2 | 5/2017 | Frey et al. |
| 9,649,170 B2 | 5/2017 | Park et al. |
| 9,655,729 B2 | 5/2017 | Parisi et al. |
| 9,662,214 B2 | 5/2017 | Li et al. |
| 9,668,748 B2 | 6/2017 | McKinnon et al. |
| 9,668,873 B2 | 6/2017 | Winslow et al. |
| 9,675,471 B2 | 6/2017 | Bojarski et al. |
| 9,693,831 B2 | 7/2017 | Mosnier et al. |
| 9,715,563 B1 | 7/2017 | Schroeder |
| 9,757,072 B1 | 9/2017 | Urbalejo |
| 9,782,228 B2 | 10/2017 | Mosnier et al. |
| 9,788,966 B2 | 10/2017 | Steinberg |
| 9,827,109 B2 | 11/2017 | Steinberg |
| 9,848,922 B2 | 12/2017 | Tohmeh et al. |
| 9,968,408 B1 | 5/2018 | Casey et al. |
| 9,987,048 B2 | 6/2018 | Mosnier et al. |
| 9,993,177 B2 | 6/2018 | Chien et al. |
| 10,010,426 B2 | 7/2018 | Kuiper et al. |
| 10,045,824 B2 | 8/2018 | Mosnier et al. |
| 10,052,135 B2 | 8/2018 | Berg et al. |
| 10,064,743 B2 | 9/2018 | Funk et al. |
| 10,092,412 B2 | 10/2018 | Drochner et al. |
| 10,098,671 B2 | 10/2018 | Augostino |
| 10,188,480 B2 | 1/2019 | Scholl et al. |
| 10,201,320 B2 | 2/2019 | Saget et al. |
| 10,219,865 B2 | 3/2019 | Jansen et al. |
| 10,292,770 B2 | 5/2019 | Ryan et al. |
| 10,314,657 B2 | 6/2019 | Mosnier et al. |
| 10,318,655 B2 | 6/2019 | Mosnier et al. |
| 10,376,182 B2 | 8/2019 | Herrmann |
| 10,413,365 B1 | 9/2019 | Mosnier et al. |
| 10,420,615 B1 | 9/2019 | Mosnier et al. |
| 10,433,893 B1 | 10/2019 | Scholl et al. |
| 10,433,912 B1 | 10/2019 | Mosnier et al. |
| 10,433,913 B2 | 10/2019 | Mosnier et al. |
| 10,441,363 B1 | 10/2019 | Mosnier et al. |
| 10,456,211 B2 | 10/2019 | McAfee |
| 10,463,433 B2 | 11/2019 | Turner et al. |
| 10,517,680 B2 | 12/2019 | Moctezuma et al. |
| 10,595,941 B2 | 3/2020 | Herrmann et al. |
| 10,736,699 B2 | 8/2020 | Ronen et al. |
| 10,777,315 B2 | 9/2020 | Zehavi et al. |
| 10,874,460 B2 | 12/2020 | Schmidt et al. |
| 2002/0035321 A1 | 3/2002 | Bucholz et al. |
| 2002/0038118 A1 | 3/2002 | Shoham |
| 2002/0045812 A1 | 4/2002 | Ben-Haim et al. |
| 2002/0103432 A1 | 8/2002 | Kawchuk |
| 2003/0191383 A1 | 10/2003 | Ben-Haim et al. |
| 2003/0204189 A1 | 10/2003 | Cragg |
| 2004/0120781 A1 | 6/2004 | Luca et al. |
| 2004/0143243 A1 | 7/2004 | Wahrburg |
| 2004/0152972 A1 | 8/2004 | Hunter |
| 2004/0167637 A1 | 8/2004 | Biscup |
| 2004/0171924 A1 | 9/2004 | Mire et al. |
| 2004/0172020 A1 | 9/2004 | Beaurain et al. |
| 2004/0215190 A1 | 10/2004 | Nguyen et al. |
| 2004/0243148 A1 | 12/2004 | Wasielewski |
| 2004/0267279 A1 | 12/2004 | Casutt et al. |
| 2005/0149050 A1 | 7/2005 | Stifter et al. |
| 2005/0177239 A1 | 8/2005 | Steinberg |
| 2005/0182320 A1 | 8/2005 | Stifter et al. |
| 2005/0182454 A1 | 8/2005 | Gharib et al. |
| 2005/0203531 A1 | 9/2005 | Lakin et al. |
| 2005/0203532 A1 | 9/2005 | Ferguson |
| 2005/0262911 A1 | 12/2005 | Dankowicz et al. |
| 2006/0015018 A1 | 1/2006 | Jutras et al. |
| 2006/0015030 A1 | 1/2006 | Poulin et al. |
| 2006/0036259 A1 | 2/2006 | Carl et al. |
| 2006/0069324 A1 | 3/2006 | Block et al. |
| 2006/0074431 A1 | 4/2006 | Sutton et al. |
| 2006/0136058 A1 | 6/2006 | Pietrzak |
| 2006/0142657 A1 | 6/2006 | Quaid et al. |
| 2006/0285991 A1 | 12/2006 | McKinley |
| 2006/0287627 A1 | 12/2006 | Johnson |
| 2007/0021682 A1 | 1/2007 | Gharib et al. |
| 2007/0118243 A1 | 5/2007 | Schroeder et al. |
| 2007/0225731 A1 | 9/2007 | Couture et al. |
| 2008/0058945 A1 | 3/2008 | Hajaj et al. |

(56) References Cited

U.S. PATENT DOCUMENTS

| | | |
|---|---|---|
| 2008/0108991 A1 | 5/2008 | von Jako |
| 2008/0177203 A1 | 7/2008 | von Jako |
| 2008/0255575 A1 | 10/2008 | Justis et al. |
| 2008/0281332 A1 | 11/2008 | Taylor |
| 2009/0024164 A1 | 1/2009 | Neubardt |
| 2009/0076615 A1 | 3/2009 | Duggal et al. |
| 2009/0157083 A1 | 6/2009 | Park et al. |
| 2009/0194206 A1 | 8/2009 | Jeon et al. |
| 2009/0204159 A1 | 8/2009 | Justis et al. |
| 2009/0248080 A1 | 10/2009 | Wilcox et al. |
| 2009/0249851 A1 | 10/2009 | Isaacs |
| 2009/0254326 A1 | 10/2009 | Isaacs |
| 2010/0042157 A1 | 2/2010 | Trieu |
| 2010/0100011 A1 | 4/2010 | Roche |
| 2010/0191071 A1 | 7/2010 | Anderson et al. |
| 2010/0191088 A1 | 7/2010 | Anderson et al. |
| 2010/0217270 A1 | 8/2010 | Polinski et al. |
| 2010/0217336 A1 | 8/2010 | Crawford et al. |
| 2011/0004309 A9 | 1/2011 | Holm |
| 2011/0071802 A1 | 3/2011 | Bojarski et al. |
| 2011/0118740 A1 | 5/2011 | Rabiner et al. |
| 2011/0172566 A1 | 7/2011 | Kawchuk |
| 2011/0214279 A1 | 9/2011 | Park et al. |
| 2011/0224796 A1 | 9/2011 | Weiland et al. |
| 2011/0257653 A1 | 10/2011 | Hughes et al. |
| 2011/0257657 A1 | 10/2011 | Turner et al. |
| 2011/0295159 A1 | 12/2011 | Shachar et al. |
| 2011/0306873 A1 | 12/2011 | Shenai et al. |
| 2012/0022357 A1 | 1/2012 | Chang et al. |
| 2012/0027261 A1 | 2/2012 | Frank et al. |
| 2012/0035611 A1 | 2/2012 | Kave |
| 2012/0123301 A1 | 5/2012 | Connor et al. |
| 2012/0143090 A1 | 6/2012 | Hay et al. |
| 2012/0150243 A9 | 6/2012 | Crawford et al. |
| 2012/0172884 A1 | 7/2012 | Zheng et al. |
| 2012/0203289 A1 | 8/2012 | Beerens et al. |
| 2013/0079678 A1 | 3/2013 | Stein et al. |
| 2013/0079679 A1 | 3/2013 | Roche et al. |
| 2013/0079790 A1 | 3/2013 | Stein et al. |
| 2013/0131486 A1 | 5/2013 | Copf et al. |
| 2013/0211531 A1 | 8/2013 | Steines et al. |
| 2013/0245631 A1 | 9/2013 | Bettenga |
| 2013/0253599 A1 | 9/2013 | Gorek et al. |
| 2013/0268007 A1 | 10/2013 | Rezach et al. |
| 2013/0303883 A1 | 11/2013 | Zehavi et al. |
| 2013/0345718 A1 | 12/2013 | Crawford et al. |
| 2014/0058407 A1 | 2/2014 | Tsekos et al. |
| 2014/0100579 A1 | 4/2014 | Kelman et al. |
| 2014/0135658 A1 | 5/2014 | Hladio et al. |
| 2014/0180415 A1 | 6/2014 | Koss |
| 2014/0194889 A1 | 7/2014 | Chang et al. |
| 2014/0228670 A1 | 8/2014 | Justis et al. |
| 2014/0228860 A1 | 8/2014 | Steines et al. |
| 2014/0244220 A1 | 8/2014 | McKinnon et al. |
| 2014/0257402 A1 | 9/2014 | Barsoum |
| 2014/0272881 A1 | 9/2014 | Barsoum |
| 2014/0277149 A1 | 9/2014 | Rooney et al. |
| 2014/0296860 A1 | 10/2014 | Stein et al. |
| 2014/0303672 A1 | 10/2014 | Tran et al. |
| 2014/0316468 A1 | 10/2014 | Keiser et al. |
| 2015/0057756 A1 | 2/2015 | Lang et al. |
| 2015/0066145 A1 | 3/2015 | Rogers et al. |
| 2015/0080901 A1 | 3/2015 | Stein |
| 2015/0081029 A1 | 3/2015 | Bojarski et al. |
| 2015/0088030 A1 | 3/2015 | Taylor |
| 2015/0100066 A1 | 4/2015 | Kostrzewski et al. |
| 2015/0100091 A1 | 4/2015 | Tohmeh et al. |
| 2015/0105782 A1 | 4/2015 | D'Lima et al. |
| 2015/0127055 A1 | 5/2015 | Dvorak et al. |
| 2015/0150646 A1 | 6/2015 | Pryor et al. |
| 2015/0164657 A1 | 6/2015 | Miles et al. |
| 2015/0182292 A1 | 7/2015 | Hladio et al. |
| 2015/0223900 A1 | 8/2015 | Wiebe, III et al. |
| 2015/0245844 A1 | 9/2015 | Kennedy et al. |
| 2015/0250597 A1 | 9/2015 | Lang et al. |
| 2015/0265291 A1 | 9/2015 | Wilkinson |
| 2015/0305878 A1 | 10/2015 | O'Neil et al. |
| 2015/0305891 A1 | 10/2015 | Bergin et al. |
| 2015/0313723 A1 | 11/2015 | Jansen et al. |
| 2015/0328004 A1 | 11/2015 | Mafhouz |
| 2015/0366630 A1 | 12/2015 | Gorek et al. |
| 2016/0000571 A1 | 1/2016 | Mahfouz |
| 2016/0007983 A1 | 1/2016 | Frey et al. |
| 2016/0015465 A1 | 1/2016 | Steines et al. |
| 2016/0022176 A1 | 1/2016 | Le Huec et al. |
| 2016/0022370 A1 | 1/2016 | Pavlovskaia et al. |
| 2016/0038161 A1 | 2/2016 | Gibson |
| 2016/0038238 A1 | 2/2016 | Kostrzewski et al. |
| 2016/0038242 A1 | 2/2016 | Lo Iacono et al. |
| 2016/0038293 A1 | 2/2016 | Slamin et al. |
| 2016/0038307 A1 | 2/2016 | Bettenga |
| 2016/0045230 A1 | 2/2016 | Lowery et al. |
| 2016/0045317 A1 | 2/2016 | Lang et al. |
| 2016/0045326 A1 | 2/2016 | Hansen et al. |
| 2016/0058320 A1 | 3/2016 | Chien et al. |
| 2016/0058523 A1 | 3/2016 | Chien et al. |
| 2016/0074052 A1 | 3/2016 | Keppler et al. |
| 2016/0074202 A1 | 3/2016 | Reed et al. |
| 2016/0081754 A1 | 3/2016 | Kostrzewski et al. |
| 2016/0095710 A1 | 4/2016 | Juszczyk et al. |
| 2016/0100907 A1 | 4/2016 | Gomes |
| 2016/0106483 A1 | 4/2016 | Mayer et al. |
| 2016/0128847 A1 | 5/2016 | Kurtaliaj et al. |
| 2016/0143744 A1 | 5/2016 | Bojarski et al. |
| 2016/0157751 A1 | 6/2016 | Mahfouz |
| 2016/0199101 A1 | 7/2016 | Sharifi-Mehr et al. |
| 2016/0228192 A1 | 8/2016 | Jansen et al. |
| 2016/0235480 A1 | 8/2016 | Scholl et al. |
| 2016/0235493 A1 | 8/2016 | LeBoeuf, II et al. |
| 2016/0242819 A1 | 8/2016 | Simpson et al. |
| 2016/0242857 A1 | 8/2016 | Scholl |
| 2016/0242934 A1 | 8/2016 | van der Walt et al. |
| 2016/0256279 A1 | 9/2016 | Sanders et al. |
| 2016/0256285 A1 | 9/2016 | Jansen |
| 2016/0262800 A1 | 9/2016 | Scholl et al. |
| 2016/0262895 A1 | 9/2016 | Shea et al. |
| 2016/0270802 A1 | 9/2016 | Fang et al. |
| 2016/0270931 A1 | 9/2016 | Trieu |
| 2016/0274571 A1 | 9/2016 | Lavallee et al. |
| 2016/0283676 A1 | 9/2016 | Lyon et al. |
| 2016/0287395 A1 | 10/2016 | Khalili et al. |
| 2016/0296285 A1 | 10/2016 | Chaoui et al. |
| 2016/0310221 A1 | 10/2016 | Bar et al. |
| 2016/0331417 A1 | 11/2016 | Trautwein et al. |
| 2016/0354009 A1 | 12/2016 | Schroeder |
| 2016/0354161 A1 | 12/2016 | Deitz |
| 2016/0360997 A1 | 12/2016 | Yadav et al. |
| 2017/0000568 A1 | 1/2017 | O'Neil et al. |
| 2017/0007145 A1 | 1/2017 | Gharib et al. |
| 2017/0007328 A1 | 1/2017 | Cattin et al. |
| 2017/0007408 A1 | 1/2017 | Fitz et al. |
| 2017/0027590 A1 | 2/2017 | Amiot et al. |
| 2017/0027617 A1 | 2/2017 | Strnad |
| 2017/0035580 A1 | 2/2017 | Murphy |
| 2017/0056179 A1 | 3/2017 | Lorio |
| 2017/0056196 A1 | 3/2017 | Kuiper et al. |
| 2017/0071503 A1 | 3/2017 | Wasielewski |
| 2017/0119316 A1 | 5/2017 | Herrmann et al. |
| 2017/0119472 A1 | 5/2017 | Herrmann et al. |
| 2017/0132389 A1 | 5/2017 | McCaulley et al. |
| 2017/0135706 A1 | 5/2017 | Frey et al. |
| 2017/0135707 A9 | 5/2017 | Frey et al. |
| 2017/0135770 A1 | 5/2017 | Scholl et al. |
| 2017/0143426 A1 | 5/2017 | Isaacs et al. |
| 2017/0143494 A1 | 5/2017 | Mahfouz |
| 2017/0143502 A1 | 5/2017 | Yadin et al. |
| 2017/0156798 A1 | 6/2017 | Wasielewski |
| 2017/0189121 A1 | 7/2017 | Frasier et al. |
| 2017/0231709 A1 | 8/2017 | Gupta et al. |
| 2017/0252107 A1 | 9/2017 | Turner et al. |
| 2017/0273718 A1 | 9/2017 | Metzger et al. |
| 2017/0323037 A1 | 11/2017 | Schroeder |
| 2017/0360493 A1 | 12/2017 | Zucker et al. |
| 2018/0092699 A1 | 4/2018 | Finley |

(56) References Cited

U.S. PATENT DOCUMENTS

| | | |
|---|---|---|
| 2018/0178148 A1 | 6/2018 | Mazor et al. |
| 2018/0256067 A1 | 9/2018 | Chien et al. |
| 2018/0289396 A1 | 10/2018 | McGahan et al. |
| 2018/0295584 A1 | 10/2018 | Gliner et al. |
| 2018/0301213 A1 | 10/2018 | Zehavi et al. |
| 2018/0303552 A1* | 10/2018 | Ryan ............... G16H 50/50 |
| 2018/0310993 A1* | 11/2018 | Hobeika ............ A61B 34/10 |
| 2018/0349519 A1 | 12/2018 | Schroeder |
| 2019/0015136 A1 | 1/2019 | Kraemer |
| 2019/0046269 A1 | 2/2019 | Hedblom et al. |
| 2019/0046287 A1 | 2/2019 | Fallin et al. |
| 2019/0059951 A1 | 2/2019 | Barrus |
| 2019/0060086 A1 | 2/2019 | Krause et al. |
| 2019/0083144 A1 | 3/2019 | Sharifi-Mehr et al. |
| 2019/0103190 A1 | 4/2019 | Schmidt et al. |
| 2019/0110819 A1 | 4/2019 | Triplett et al. |
| 2019/0117278 A1 | 4/2019 | Chin |
| 2019/0122364 A1 | 4/2019 | Zhang et al. |
| 2019/0142599 A1 | 5/2019 | Thibodeau |
| 2019/0167314 A1 | 6/2019 | Mosnier et al. |
| 2019/0167435 A1 | 6/2019 | Cordonnier |
| 2019/0201013 A1 | 7/2019 | Siccardi et al. |
| 2019/0201155 A1 | 7/2019 | Gupta et al. |
| 2019/0209080 A1 | 7/2019 | Gullotti et al. |
| 2019/0209212 A1 | 7/2019 | Scholl et al. |
| 2019/0223916 A1 | 7/2019 | Barrus et al. |
| 2019/0231443 A1 | 8/2019 | McGinley et al. |
| 2019/0231557 A1 | 8/2019 | Sutterlin, III et al. |
| 2019/0239935 A1 | 8/2019 | Willis et al. |
| 2019/0247100 A1 | 8/2019 | Mundis, Jr. et al. |
| 2019/0254769 A1 | 8/2019 | Scholl et al. |
| 2019/0262015 A1 | 8/2019 | Siccardi et al. |
| 2019/0269463 A1 | 9/2019 | Mosnier et al. |
| 2019/0343587 A1 | 11/2019 | Mosnier et al. |
| 2019/0362028 A1 | 11/2019 | Mosnier et al. |
| 2019/0380782 A1 | 12/2019 | McAfee et al. |
| 2020/0038109 A1* | 2/2020 | Steinberg ............... G16H 50/50 |
| 2020/0060768 A1 | 2/2020 | Mosnier et al. |
| 2020/0121394 A1 | 4/2020 | Mosnier et al. |
| 2020/0297424 A1 | 9/2020 | Helm et al. |
| 2020/0297425 A1 | 9/2020 | Helm et al. |
| 2020/0315708 A1 | 10/2020 | Mosnier et al. |
| 2020/0345420 A1 | 11/2020 | Hobeika et al. |
| 2021/0059822 A1 | 3/2021 | Casey et al. |
| 2021/0145518 A1 | 5/2021 | Mosnier et al. |
| 2021/0244447 A1* | 8/2021 | Schroeder ............. B33Y 80/00 |
| 2022/0160428 A1* | 5/2022 | Murray ............. A61B 17/7086 |

FOREIGN PATENT DOCUMENTS

| | | |
|---|---|---|
| WO | 2019043426 A1 | 3/2019 |
| WO | 2019148154 A1 | 8/2019 |
| WO | 2019217824 A1 | 11/2019 |
| WO | 2022269345 A1 | 12/2022 |

OTHER PUBLICATIONS

Written Opinion in Application No. PCT/IB2022/000331 mailed Nov. 25, 2022.

"Predicting 3D Thoracic Kyphosis Using Traditional 2D Radiographic Measurements in Adolecent Idiopathic Scoliosis," by Kevin Parvaresh, MD, Spine Deformity 5 (2017) 159-165.

"Compensatory Spinopelvic Balance Over the Hip Axis and Better Reliability in Measuring Lordosis to the Pelvic Radius on Standing Lateral Radiographs of Adult Volunteers and Patients," Roger P. Jackson MD, et al., Spine vol. 23, No. 16, pp. 1750-1767, copyright 1998, Lippincott Williams & Wilkins.

"Postoperative Changes in Spinal Rod Contour in Adolescent Idiopathic Scoliosis, An in Vivo Deformtion Study," by Krishna R. Cidambi, MD et al., Spine vol. 37, No. 18, pp. 1566-1572, copyright 2012, Lippincott Williams & Wilkins.

Renaud Lafage, et al., Surgical Planning for Adult Spinal Deformity: Anticipated Sagittal Alignment Corrections Accordings to the Surgical Level, Global Spine Journal, sagepub.com/journals-permissions, DOI: 10.177/2192568220988504 journals.sagepub.com/home/gsj © The Authors(s) 2021, pp. 1-9.

* cited by examiner

114

| DESIGNING FIRST ROD GEOMETRY FOR SELECTED VERTEBRAE | — 302 |

| APPROXIMATE BEND OUT OF FIRST ROD | — 304 |

| PERFORM DIFFERENCE BENDING OF SECOND ROD | — 306 |

SYSTEMS AND METHODS FOR PLANNING A PATIENT-SPECIFIC SPINAL CORRECTION

FIELD

The present technology is generally related to systems and methods for planning a patient-specific spinal correction surgery and/or conducting a surgery.

BACKGROUND

Spinal disorders such as adolescent idiopathic scoliosis, degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders or deformities typically result in symptoms including pain, nerve damage, and partial or complete loss of mobility, at a minimum. In adolescence, spinal deformity may affect lung capacity and other bodily functions.

Spinal surgery may involve implantation of one or more spinal implants, such as a spinal rod, to correct the curvature of the spine of a patient and to prevent further deterioration. In adolescent idiopathic scoliosis, concaved and convex spinal rods of particular curvatures are used. These spinal rods, however, can deform based on in vivo impact forces. The spinal rod curvature can be a key factor in the treatment of a spinal deformity.

This disclosure describes an improvement over these prior art technologies.

SUMMARY

The techniques of this disclosure generally relate to systems and methods for planning a patient-specific spinal correction that may include designing a patient-specific spinal implant based on a three-dimensional (3D) nature of a deformity, for example, to correct a patient-specific adolescent idiopathic scoliosis (AIS) deformity, such as by designing a rod contour that accounts for rod deformation and/or bending out to achieve a thoracic kyphosis goal for use in treating the deformity.

In one aspect, the present disclosure provides a method to plan a spinal correction surgery. The method includes, for example, measuring spinal parameters of a spine in a two-dimensional (2D) pre-operative spinal image including at least a pre-operative thoracic Cobb angle and a pre-operative thoracic kyphosis and transforming the 2D pre-operative spinal image to a three-dimensional (3D), pre-operative spinal image representation. The transforming may include performing segmentation of spine elements in the 2D pre-operative spinal image, and applying a mathematical formula based on the thoracic Cobb angle and the thoracic kyphosis to the spine elements. The method includes identifying a thoracic kyphosis goal having a post-operative thoracic kyphosis value to a selected set of the spine elements, transforming a gap of the spine elements representative of a difference between the pre-operative thoracic kyphosis in 3D pre-operative spinal image representation and the thoracic kyphosis goal to create a 3D post-operative spinal image representation, and determining a first rod design based on the 3D post-operative spinal image representation to achieve the post-operative thoracic kyphosis value in the selected set of spine elements.

In another aspect, the disclosure provides a system that includes, for example, at least one processor and a non-transitory and tangible computer readable storage medium having programming instructions stored thereon, which when executed cause the at least one processor to measure spinal parameters of a spine in a two-dimensional (2D) pre-operative spinal image including at least a pre-operative thoracic Cobb angle and a pre-operative thoracic kyphosis; and transform the 2D pre-operative spinal image to a three-dimensional (3D), pre-operative spinal image representation. The processor may, for example, transform the 2D image by: performing segmentation of spine elements in the 2D pre-operative spinal image; and applying a mathematical formula based on the thoracic Cobb angle and the thoracic kyphosis to the spine elements. The processor, for example, may also identify a thoracic kyphosis goal having a post-operative thoracic kyphosis value to a selected set of the spine elements, transform a gap of the spine elements representative of a difference between the pre-operative thoracic kyphosis in 3D pre-operative spinal image representation and the thoracic kyphosis goal to create a 3D post-operative spinal image representation, and determine a first rod design based on the 3D post-operative spinal image representation to achieve the post-operative thoracic kyphosis value in the selected set of spine elements.

In another aspect, the disclosure provides a method, for example, that includes planning a surgery to correct a spinal deformity and obtaining a rod formed of biocompatible material configured to approximate a first rod design. The method may include during surgery, bending the rod with a rod bending device to create the first rod design; and implanting the bent rod.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
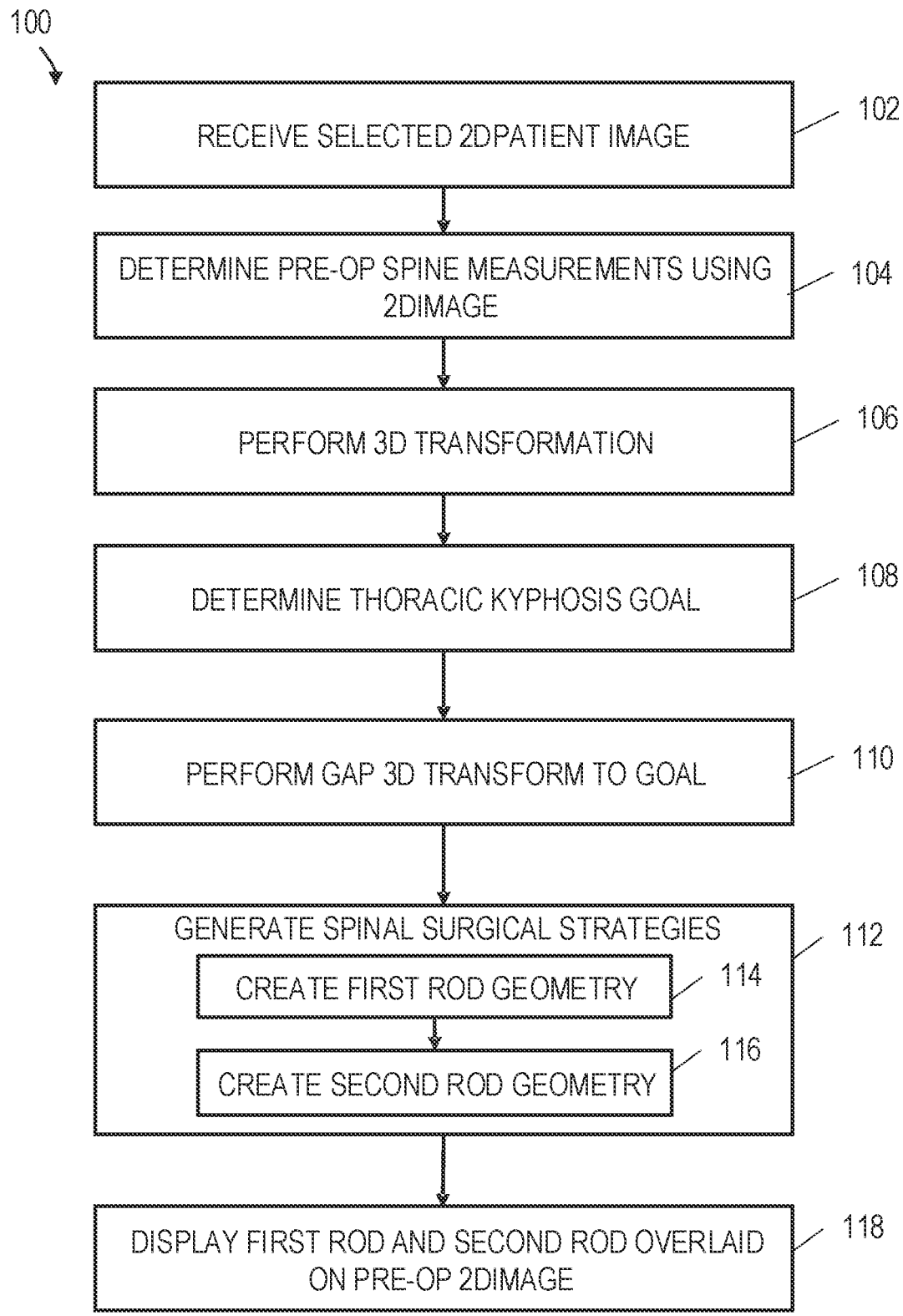
FIG. 1 is a flowchart that illustrates an example method for planning a patient-specific spinal correction.

The embodiments described herein relate to systems and methods for planning a patient-specific spinal correction that may include designing a patient-specific spinal implant based on a three-dimensional (3D) nature of a deformity, for example, to correct a patient-specific adolescent idiopathic scoliosis (AIS) deformity, such as by designing a rod contour that accounts for rod deformation and/or bending out to achieve a thoracic kyphosis goal for use in treating the deformity.

In particular, some embodiments described herein are directed to the design and/or manufacture of patient-specific spinal rods. In some embodiments, the systems and methods described herein may be configured to design and/or produce a patient-specific spinal rod for use in a surgical procedure to correct a spinal deformity.

The planning system of the present disclosure may be understood more readily by reference to the following detailed description of the embodiments taken in connection with the accompanying drawing figures that form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, front, back, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition may refer to planning for and performing a procedure that may include administering one or more drugs to a patient (human or other mammal), employing implantable devices, and/or employing instruments that treat the disease, such as, for example, instruments used to implant bone constructs, pedicle screws, and spinal rods, for example.

Alleviation can occur prior to signs or symptoms of the disease or condition appearing, as well as after their appearance. Thus, treating or treatment includes preventing or prevention of and/or reducing the likelihood of a certain disease or undesirable condition (e.g., preventing or reducing the likelihood of the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a computing system for generating a model of a three-dimensional (3D) nature of a patient-specific deformity, planning a correction of the patient-specific deformity and/or for designing a rod contour with a degree of bending out. The following disclosure includes a description of computer-implemented methods of employing the computing system in accordance with the principles of the present disclosure. Alternate embodiments are also disclosed. Reference is made in detail to the exemplary embodiments of the present disclosure, which are illustrated in the accompanying figures.

The designed implant rod may be fabricated from biologically acceptable materials suitable for medical applications, including computer aided metals, computer aided plastics, metals, synthetic polymers, ceramics and bone material and/or their composites. For example, the rod may be fabricated from materials such as stainless steel alloys, aluminum, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologic, Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The rod may have material composites, including the above materials, to achieve various desired characteristics such as strength, rigidity, elasticity, compliance, biomechanical performance, durability and radiolucency or imaging preference. The rod may also be fabricated from a heterogeneous material such as a combination of two or more of the above-described materials. The rod may be monolithically formed.

This disclosure incorporates herein by reference in its entirety U.S. Ser. No. 17/130,492, entitled "SYSTEMS, METHODS, AND DEVICES FOR DEVELOPING PATIENT-SPECIFIC SPINAL IMPLANTS, TREATMENTS, OPERATIONS, AND/OR PROCEDURES."

The method steps described herein may be performed in the order shown or a different order. One or more method steps may be performed contemporaneously. One or more method steps may be added or deleted.

FIG. 1 is a flowchart that illustrates an example method 100 for planning a patient-specific spinal correction of a deformity. The method may be a computer-implemented method with one or more graphical user interfaces (GUIs) that may be configured to interact with the user and display on a display device (FIG. 11) the resultant output data, for example, as will be described in relation to FIGS. 6A-10. The method 100 will be described also in relation to the surgery planning system described in more detail in FIG. 11.

The method 100 may include (at 102) receiving, by at least one processor 1105 (FIG. 11), a selected two-dimensional (2D) patient image. One or more medical imaging techniques may be used to capture a patient's spinal deformity or disease, for example. The imaging technique may include a 2D imaging technique, such as, fluoroscopy, computerized tomography (CT) scan and magnetic resonance imaging (MRI), for example. The surgery planner (hereinafter referred to as "user") selects a 2D patient image of the spine for which to begin the planning a surgical procedure for a spinal correction. The 2D patient image may be selected from one or more 2D patient images of the coronal plane and/or sagittal plane, by way of non-limiting example, of the spine. The 2D images may include lateral views and anteroposterior view, for example. The method 100 may include (at 102) receiving more than one selected 2D patient image. The 2D patient images may be displayed to the user for selecting using a user interface, such as a keyboard, a touchscreen display, a mouse, or a stylus.

The method 100 may include (at 104) determining, by at least one processor 1105, 2D spine measurements based on the 2D patient image. For example, the 2D measurements may include one or more of pre-op values, such as, sagittal Cobb (SCobb) angle, coronal Cobb (CCobb) angle, thoracic Cobb (TCobb) angle, lumbar Lordis (LL), pelvic incidence (PI), thoracic kyphosis (TK), sacaral slope (SS) and pelvic tilt (PT), for example. The 2D spine measurements are pre-operation (pre-op) measurements. The 2D spine measurements may include a sagittal vertical axis (SVA) pre-op value, for example. The image data may be analyzed using machine-learning algorithms 1123 to perform one or more spine measurements 1161 (FIG. 11).

Figure 5:
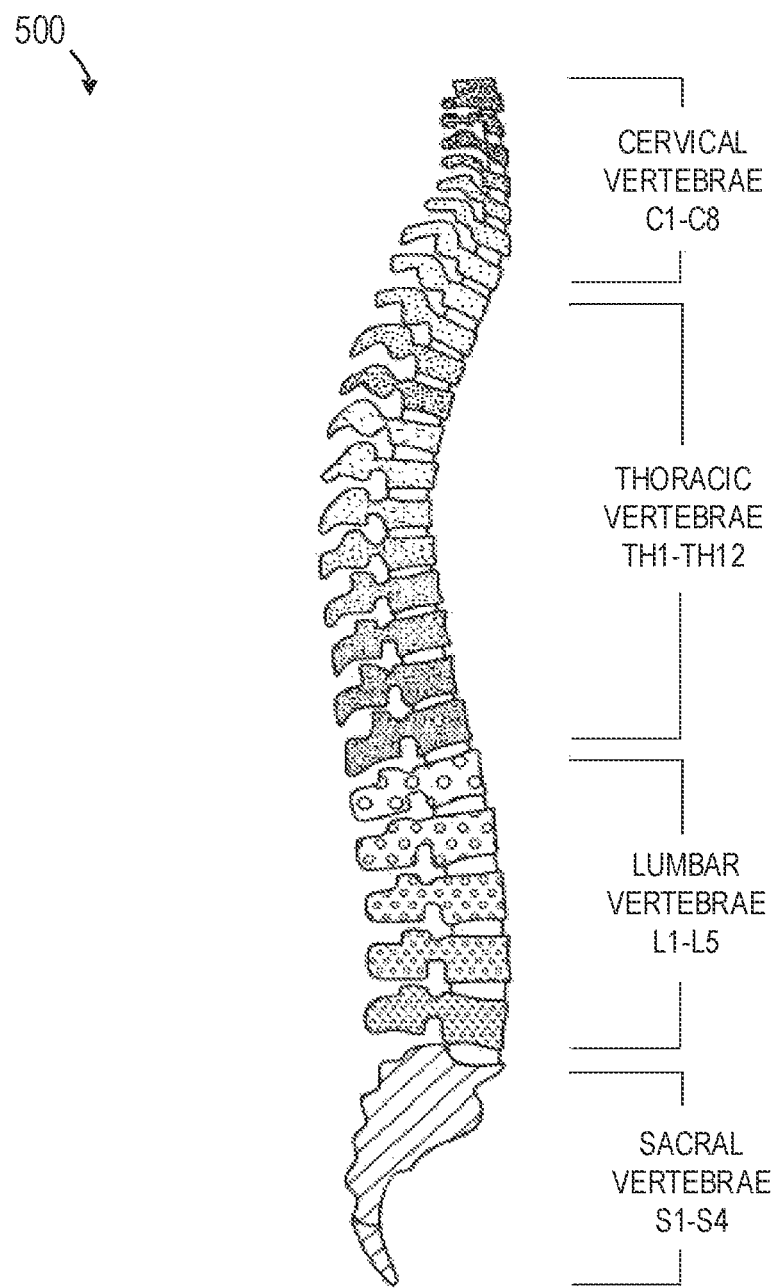
FIG. 5 is an example illustration of a spine.

FIG. 5 is an example illustration of a spine 500. The spine 500 may include cervical vertebra C1-C8, a thoracic vertebra TH1-TH12, a lumbar vertebra L1-L5, a sacral vertebra S1-S4 or other part along the vertebral column of the patient. The reference nomenclature "C #" includes a C to denote the cervical section of the spine and # represents the level of the cervical section. The reference nomenclature "TH #" includes a TH to denote the thoracic section of the spine and # represents the level of the thoracic section. The reference nomenclature "L #" includes a L to denote the lumbar section of the spine and # represents the level of the lumbar section. The reference nomenclature "S #" includes a S to denote the sacral section of the spine and # represents the level of the sacral section.

When performing 2D spine measurements based on the 2D patient image (at 104), the at least one processor 1105, may be configured to perform segmentation 1160 (FIG. 11) of objects in the 2D image, label or classify the objects and define the objects boundaries. Segmentation of objects is generally understood by one skilled in the art, may be to label or identify objects within the image, such as, each level of the spine.

Figure 11:
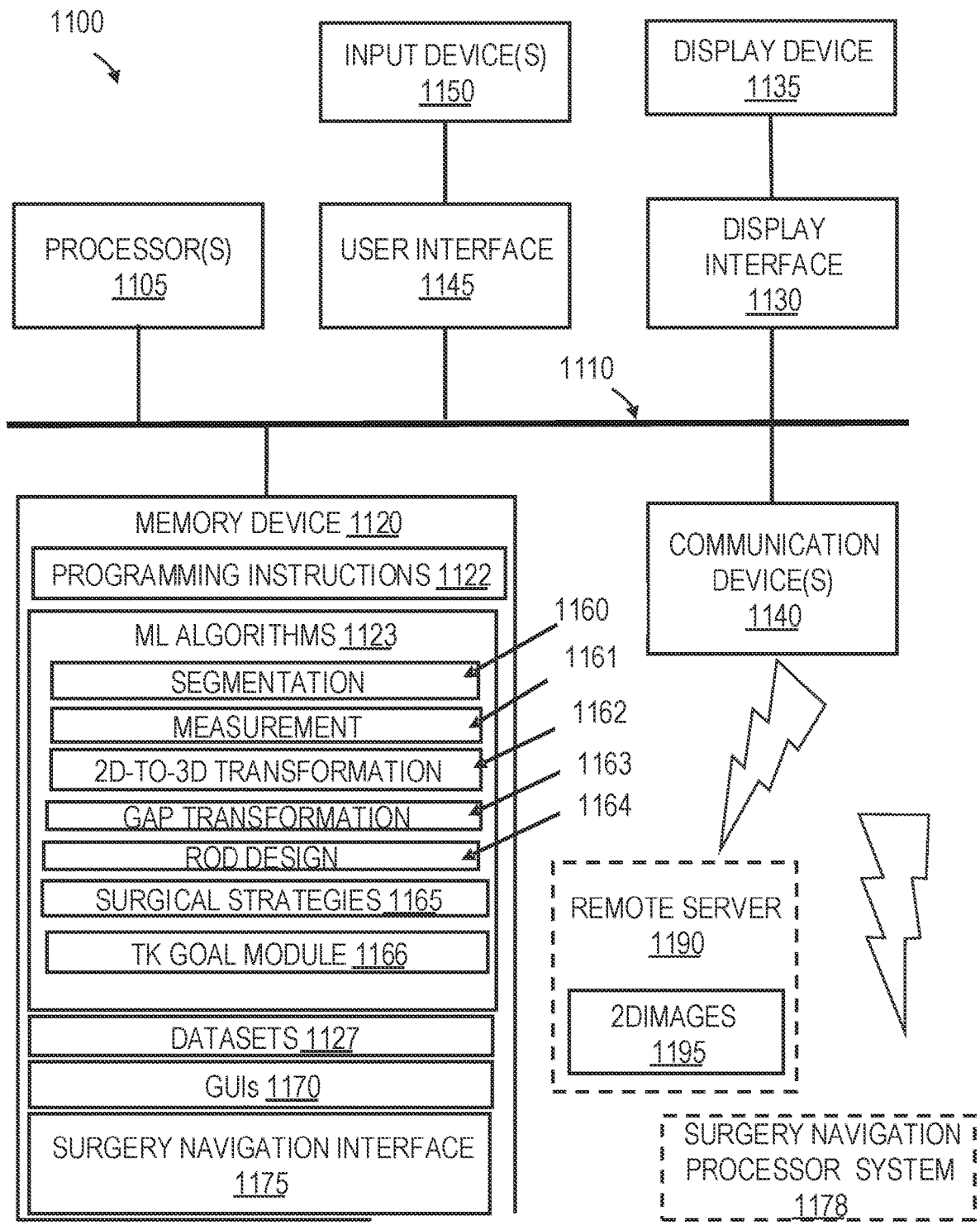
FIG. 11 illustrates an example of internal hardware that is included in any of the electronic components of an external electronic device.

In some embodiments, the at least one processor 1105 when performing one or more steps, such as without limitation, segmentation of images, may be configured to utilize machine-learning algorithms 1123 (FIG. 11) stored in memory device 1120 (FIG. 11). The machine-learning algorithms 1123 may include one or more of a Generative Adversarial Network (GAN) algorithm, a Convolutional Neural Network (CNN) algorithm, and/or a Recurrent Neural Network (RNN) algorithm, linear regression, Support Vector Machine (SVM) algorithm, Support Vector Machine-Regression (SVR) algorithm, and/or any combination thereof. For example, in some embodiments, the at least one processor 1105 may be configured to utilize a combination of a CNN algorithm with an SVM algorithm.

Figure 6A:
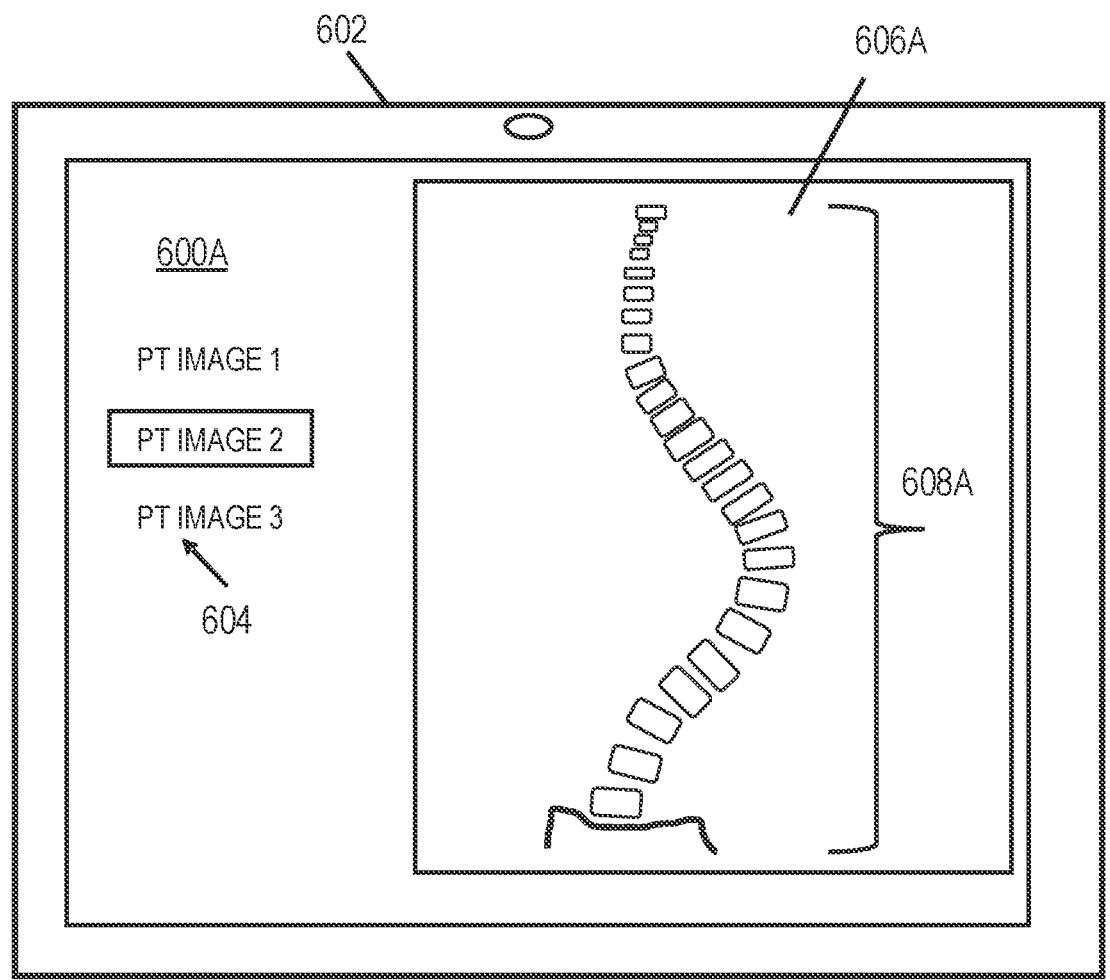
FIG. 6A is an example illustration of a graphical user interface (GUI) displaying a 2D patient image of the spine.

FIG. 6A is an example illustration of a GUI 600A displayed on a display device 602 and a selected 2D patient image 606A of the spine 608A. The GUI 600A may include a list of patient file names 604 associated with at least one uploaded 2D patient image. In this example, there are three uploaded 2D patient images. The displayed image 606A may be an anteroposterior standing view of the patient. The second entry in the list is selected, as denoted by a dotted-hatched box. In this view, the 2D patient image 606A may be represented as a segmented spinal column with each vertebra segmented. The sacral section may also be segmented.

In some embodiments, when determining pre-op spine measurements (at 104), the at least one processor 1105 may be configured to receive, access, and/or obtain one or more other pre-op radiographic parameters or values as well, such as Central Sacral Vertical Line (CSVL), C2TH1 Pelvic Angle)(CTPA,°), C2C7 SVA (mm) (Sagittal Vertical Axis), Cervical Lordosis, Lenke Classification, Proximal Junctional Kyphosis (PJK), sacral slope (SS), TH1 Slope)(TH1S, °) TH1 Tilt Angle and Direction, TH1O-L2 angle, TH12-S1 Lumbar Lordosis (LL), TH1-TH12, TH2-TH12, TH2-TH5, TH5-TH12 Thoracic Kyphosis, Thoracic (TH) Apex, Th Curves/Cobb angles, TH Curve Levels, (TH/L Lumbar Apex, TH/L Lumbar Curve, TH/L Lumbar Curve Direction of curve, TH/L Lumbar Curve Levels), TH1 Pelvic Angle (TPA), Anatomical Kyphosis, Anatomical Lordosis, Cobb Angles, Coordinates of all vertebra corners in the sagittal and/or coronal planes and the femoral heads, and any other pre-operative data like, Computerized tomography Performed, Tri-Radiate Cartilage, External Auditory Meadus, Pelvic Obliquity, Acetabular Index, and/or the like.

Figure 6B:
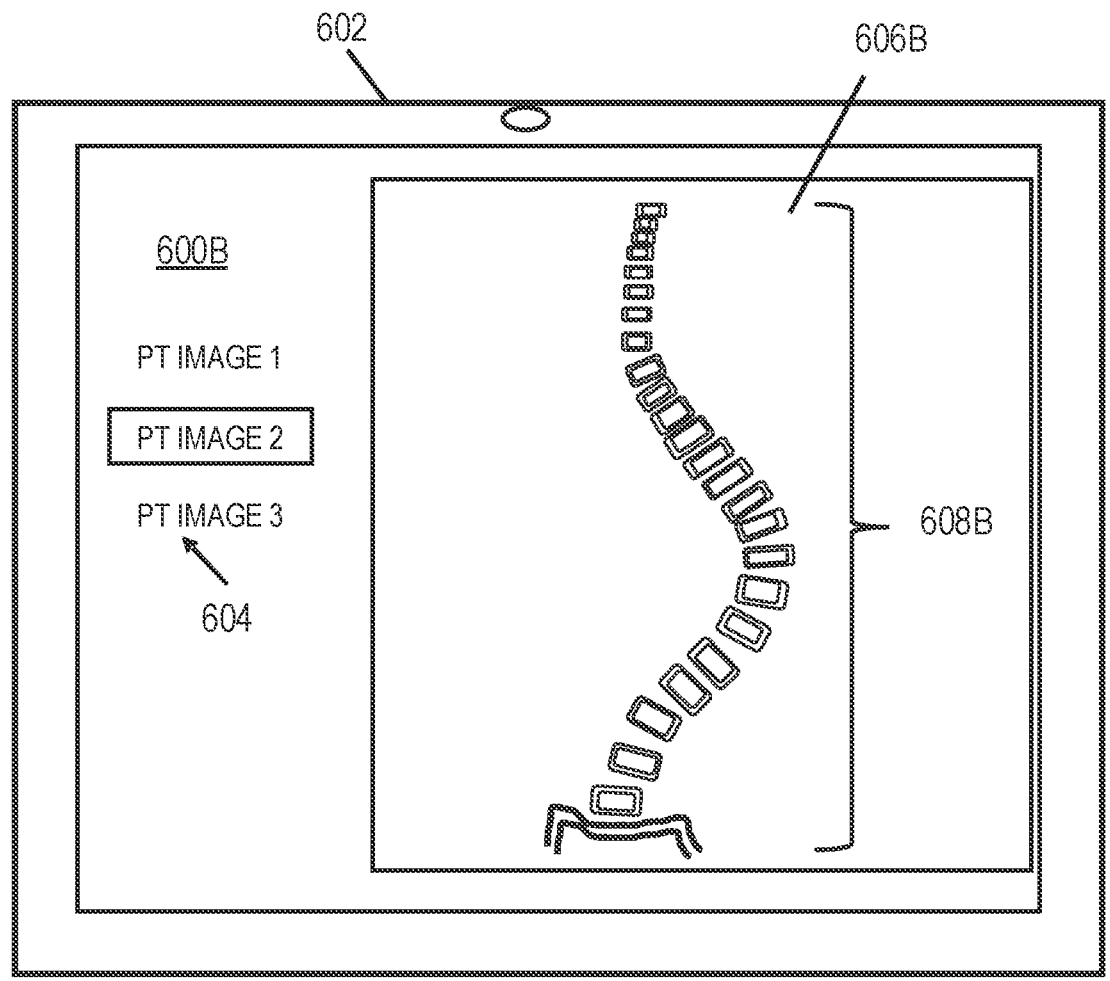
FIG. 6B is an example illustration of a graphical user interface (GUI) displaying 3D patient image of the spine.

The method 100 may include (at 106) performing, by at least one processor 1105, a 3D transformation of the 2D spinal image representation to a 3D spinal image representation, such as for display on a display device. FIG. 6B is an example illustration of a GUI 600B displaying 3D spinal image 606B representation of the spine 608B.

When performing the 3D transformation (at 106), the at least one processor 1105 may be configured to apply a mathematical formula representative of a 3D transformation to the 2D spinal image representation and generate the 3D spinal image 606B representation, as will be described in more detail in relation to FIG. 2. The method 100 may include (at 106) repeating the performing a 3D transformation of the 2D spinal image representation to a 3D spinal representation, for each received 2D patient image. For example, the received 2D patient image may include a selection of a plurality of 2D patient images to be used in determining the thoracic kyphosis goal and/or for 3D transformation. The at least one processor 1105 may be configured to output and cause display of the 3D transformation indicative of the 3D spinal image 606B representation in the GUI 600B.

Figure 2:
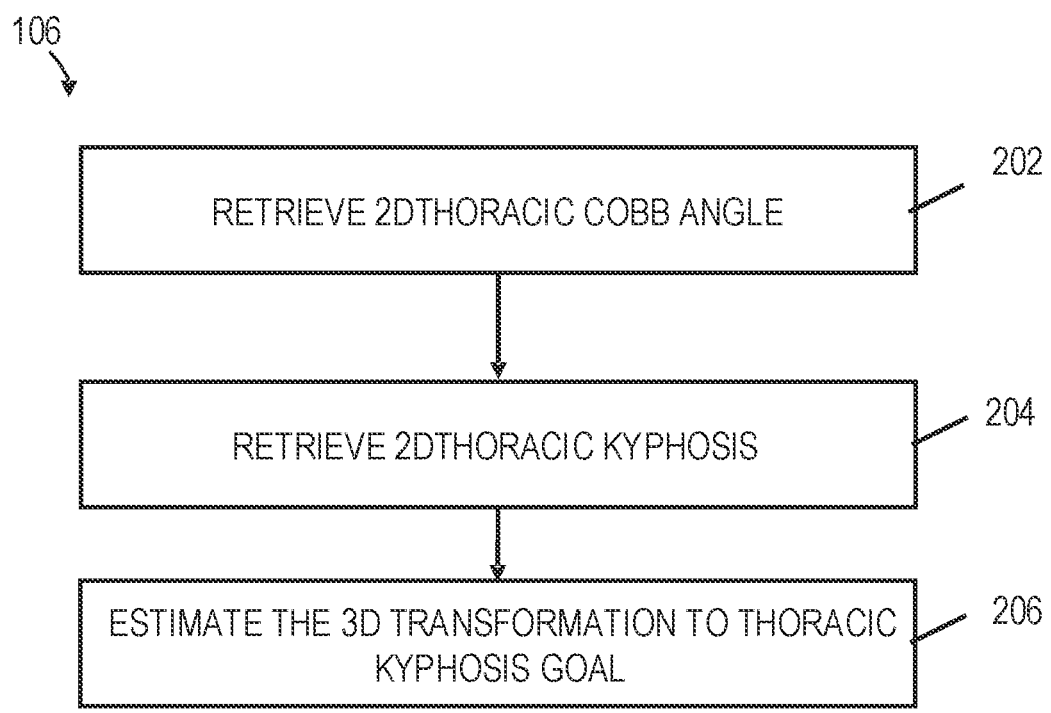
FIG. 2 is a flowchart that illustrates an example method for three-dimensional (3D) transformation from the two-dimensional (2D) spinal representation to a 3D spinal representation.
Figure 7A:
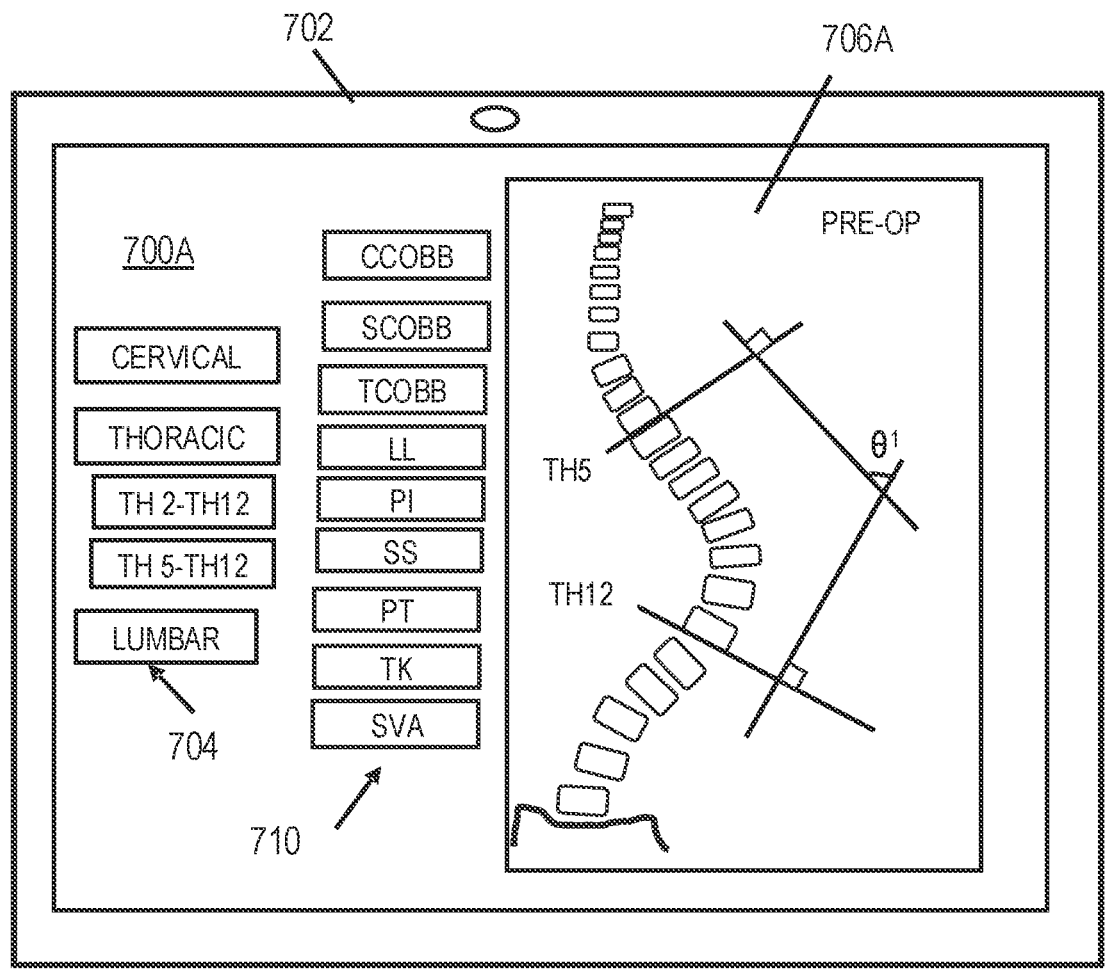
FIG. 7A is an example illustration of a graphical user interface (GUI) displaying a measurement of a pre-operative thoracic kyphosis.

FIG. 2 is a flowchart that illustrates an example method for 3D transformation from the two-dimensional (2D) spinal representation to a 3D spinal representation (hereinafter sometimes referred to as 2D-to-3D transformation). The method 104 may include (at 202) retrieving the calculated 2D thoracic Cobb (2D TCobb) angle and (at 204) retrieve the calculated 2D thoracic kyphosis (2D TK). An example, 2D thoracic kyphosis between TH5-TH12 is shown in FIG. 7A. Cobb angles may be determined based on other combination of thoracic vertebrae, cervical vertebrae, lumbar vertebrae and/or sacral vertebrae, as is generally understood in the art. The method 104 may include (at 206) estimating the 3D transformation from a standard 2D measurement in degree. In some embodiments, the 3D transformation estimation may be expressed in equation (EQ1) defined as:

$$18.1+(0.81*2D\ TK)-(0.54*2D\ TCobb\ angle) \qquad EQ1,$$

as described in "Predicting 3D Thoracic Kyphosis Using Traditional 2D Radiographic Measurements in Adolescent Idiopathic Scoliosis," by Kevin Parvaresh, MD, Spine Deformity 5 (2017) 159-165, incorporated herein by reference in its entirety.

In certain embodiments, the method may include receiving, accessing, and/or obtaining one or more radiographic parameters, such as for example, pre-operative data such as TH4-TH12 Thoracic Kyphosis (TK), L1-S1 Lumbar Lordosis (LL), Sagittal Vertical Axis (SVA), Pelvic Tilt (PT), Pelvic Incidence (PI), Lordosis, and/or the like.

In some embodiments, a first set of input values for pre-operative and/or post-operative data may include one or more of the following: TH4-TH12 TK, L1-S1 LL, SVA, Lowermost Instrumented Vertebrae (LIV), Uppermost Instrumented Vertebrae (UIV), Pelvic Tilt, Age at the time of surgery, and/or Pelvic Incidence (PI). The at least one processor 1105 may be configured to perform the 2D-to-3D transformation 1162 using one or more machine-learning algorithms described herein.

FIG. 7A is an example illustration of a GUI 700A displaying on a display device 702 a measurement of a pre-operative thoracic kyphosis (TK), denoted as angle $\theta^1$. The thoracic kyphosis may be measured as an angle of intersection of a selected or identified set of thoracic vertebrae. The GUI 700A includes a list of spinal sections 704 for the illustrated 2D spinal image representation 706A. The thoracic section is shown selected, as denoted by the dotted hatched box. Below the thoracic section there includes a menu for selecting, for example, thoracic vertebrae TH2-TH12 and TH5-TH12, for example. In this example, the levels 5-12 of the thoracic section are selected, as denoted by a dotted hatched box. The at least one processor 1105 may be configured to cause the display device 702 to display other pre-op measurements. The GUI 700A may include buttons 710 for selecting, by a user, a pre-operative measurement, such as without limitation, CCobb angle, SCobb angle, TCobb angle, LL, PI, SS, PT, TK and SVA. In this example, the TK angle $\theta^1$ is selected and displayed. The levels may be selected by a user or automatically by the at least one processor.

Figure 7B:
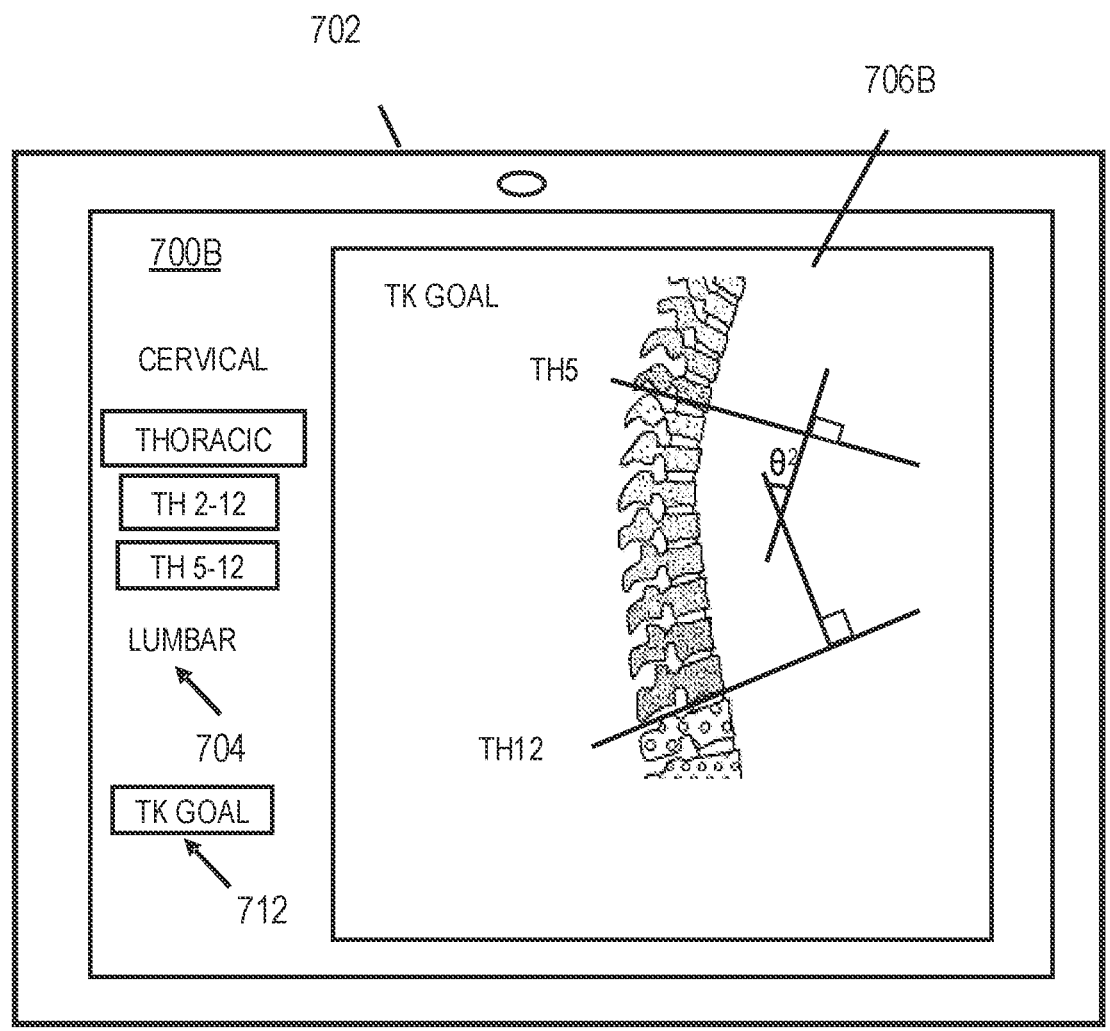
FIG. 7B is an example illustration of a graphical user interface (GUI) displaying a thoracic kyphosis goal.

The method may include (at 108), by at least one processor 1105, determining a thoracic kyphosis goal, and example is shown in FIG. 7B. In some embodiments, the thoracic kyphosis goal may be identified by the surgeon or by a set of identified preferences of a surgeon. The thoracic kyphosis goal may be used to plan the surgery to achieve the spine correction goal. The thoracic kyphosis goal may be measured as an angle of intersection with a selected set of thoracic vertebrae. For example, the goal may correct TH5-TH12. In other example, the goal may correct a combination of vertebrae from TH2-TH12.

FIG. 7B is an example illustration of a GUI 700B displaying a thoracic kyphosis goal of $\theta^2$. In this example, the thoracic kyphosis goal may be entered via the GUI 700B using data field 712. In other embodiments, a range may be provided to the user using the GUI 700B from which a goal may be selected. The thoracic kyphosis goal of $\theta^2$ may be identified in an image 706B on the GUI 700B. The image 706B illustrates the thoracic kyphosis goal as a function of the selected vertebrae for correction, such as TH5-TH12, for example.

In some embodiments, when determining a thoracic kyphosis goal, at least one processor 1105, (at 108) may be configured to select one or more input parameters, for example, age, PI pre-op value, PT pre-op value, LL pre-op value, TK pre-op value, SVA pre-op value, lower instrumented level, upper instrumented level, LL post-op target value, surgeon, weight, shape of the pre-operative spine, pre-operative x-ray, or the like. In some embodiments, the at least one processor 1105 may be configured to standardize the range of input parameters and/or utilize a scaling methodology for displaying on a display device using one or more GUIs. The at least one processor 1105 may be configured to allow a vertebrae range to be selected either by input fields or by selecting (marking) first and second locations on the image representative of the selected set of vertebrae to achieve the thoracic kyphosis goal.

The thoracic kyphosis goal may be determined using machine-learning algorithms 1123, by at least one processor 1105. In some embodiments, the method 100, when determining a thoracic kyphosis goal (at 108), may include generating, by the at least one processor 1105, a predictive model for determining post-operative parameters, such as for example thoracic kyphosis and/or pelvic tilt, using a thoracic kyphosis goal module 1166 and datasets 1127, for example. The generating may include accessing a dataset 1127 (FIG. 11) in an electronic database, the dataset 1127 may include data about the patient (for example, an X-ray images or clinical information) and the surgery strategy (for example, upper instrumented vertebra, lower instrumented vertebra, bending device, rod cutting parameter, or the like). In some embodiments, method 100 may include defining in the dataset 1127, which parameters should be inputs of the model and which parameters should be outputs of the model. For example, outputs of the model may include the parameters that the system (e.g., at least one processor 1105) may be configured to predict the thoracic kyphosis goal for the treatment of the patient based on the pre-op spine measurements.

The method may include (at 110), by at least one processor 1105, performing a gap 3D transform to represent the patient's 3D model of the spine corrected to the thoracic kyphosis goal. In some embodiments, the total mean thoracic kyphosis may be 47° for adults, for example, as described in "Compensatory Spinopelvic Balance Over the Hip Axis and Better Reliability in Measuring Lordosis to the Pelvic Radius on Standing Lateral Radiographs of Adult Volunteers and Patients," Roger P. Jackson MD, et al., SPINE Vol. 23, No. 16, pp. 1750-1767, copyright 1998, Lippincott Williams & Wilkins, incorporated herein by reference in its entirety. By way of non-limiting example, the adolescent patient may be corrected to conform to an adult total thoracic kyphosis. The total mean thoracic kyphosis in degrees may be calculated based on the total kyphosis from TH1-TH12 based on the Cobb method.

The gap 3D transformation may be determined using machine-learning algorithms 1123, by at least one processor 1105, using a predicted model of the gap transformation 1163 and related datasets 1127. The datasets 1127 may be trained based on radiological analysis of patients having a similar deformity. The dataset 1127 may include training data to train the machine-learning algorithms.

Figure 8:
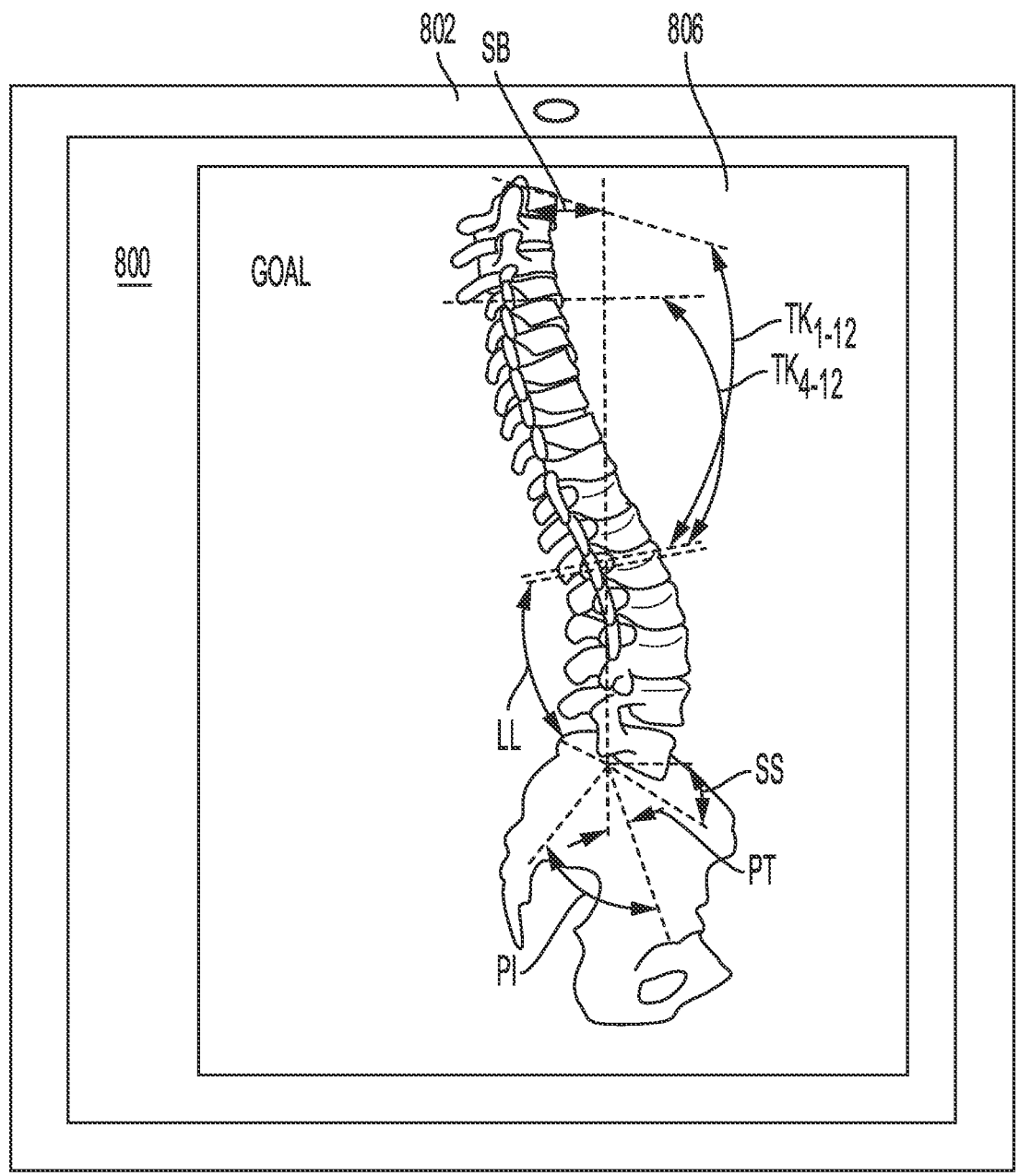
FIG. 8 is an example illustration of a graphical user interface (GUI) displaying resultant 3D image of a 3D gap transformation to the goal.

FIG. 8 is an example illustration of a GUI 800 displaying a resultant 3D image 806 of a 3D gap transformation to the goal by a display device 802. The method 100, when performing a gap 3D transform to the goal (at 110), may include, by at least one processor 1105, analyzing one or more 3D pre-operative medical images of a spine of a patient, as shown in FIG. 6B, to determine one or more pre-operative spinopelvic parameters. The one or more spinopelvic parameters may include one or more of lumbar lordosis (LL), pre-operative thoracic kyphosis (TK), pelvic incidence (PI), pelvic tilt (PT), or sagittal vertical axis (SVA) for one or more vertebrae. The system may be configured to train a predictive model and/or generate one or more post-operative predictions, for example using one or more machine learning techniques or neural networks. In FIG. 8, the pre-operative spine may be transformed to the post-operative spine in a 3D image representation. The resultant goals of the spinal column is shown. The goals include post-operative measurements for a TK from levels 1-12, a TK from levels 4-12, a LL, SS, PT, PI and sagittal balance (SB). The sagittal vertical axis may be used in lieu of the sagittal balance.

The 3D transforming, by the at least one processor 1105, may include determining one or more 3D pre-operative spinopelvic parameters to obtain one or more pre-operative spinopelvic parameters in a frequency domain. The transforming may include applying a Fourier transformation to the determined one or more pre-operative spinopelvic parameters, filtering, using at least one processor 1105, the one or more pre-operative spinopelvic parameters in the frequency domain. The filtering may include filtering out one or more of the one or more pre-operative spinopelvic parameters in the frequency domain including a frequency level above a predetermined threshold. The transforming may include applying, using at least one processor 1105, one or more predictive models to generate a predicted surgical outcome in the frequency domain based at least in part on the filtered one or more pre-operative spinopelvic parameters in the frequency domain and the one or more pre-operative non-imaging data of the subject. The one or more predictive models may include one or more of a generative adversarial network (GAN) algorithm, convolutional neural network (CNN) algorithm, or recurrent neural network (RNN) algorithm. The transforming, using at least one processor 1105, may transform the generated predicted surgical outcome in the frequency domain to obtain a generated predictive surgical outcome in a spatial domain. The transforming of the generated predicted surgical outcome in the frequency domain may include applying an inverse Fourier transformation to the generated predicted surgical outcome in the frequency domain, and generating a patient-specific spinal treatment based at least in part on the generated predictive surgical outcome in the spatial domain. The generated patient-specific spinal treatment may include one or more patient-specific spinal surgical procedures.

The method 100 may include (at 112) determining or generating, by at least one processor 1105, spinal surgical strategies including one or more surgical data parameters, such as Instrumentation Material, Instrumentation Size, Instrumentation Type, Minimal Invasive Surgery (MIS) options, Number of instrumented Levels, Osteotomies Performed, Rod Bending shapes and/or Angles, Rod Cutting Parameters, Uppermost Instrumented Parameters, Upper Instrumented Vertebrae (UIV), Lower Instrumented Vertebrae (LIV), Surgeon, surgical techniques (in some embodiments, using one or more machine learning algorithms to analyze surgeon's surgical techniques to be able to simulate the surgery and the rod that will match surgeon's expectations), radiography as an image, scanner, MRI (image or set of images), and/or the like. The machine-learning algorithms 1123, for surgical strategies 1165 may employ supervised machine learning, semi-supervised machine learning, unsupervised machine learning, deep learning and/or reinforcement machine learning. Each of these listed types of machine-learning algorithms is well known in the art.

In various embodiments computer-aided design programming applications may be used to draw or trace a rod geometric design. The particular type of drawing software utilized is not dependent on the system as the system may, irrespective of the particular platform or software utilized, generate manufacture or machine drawings to manufacture a rod.

The method 100 may include (at 112) creating, by at least one processor 1105, a first rod geometry (at 114) and/or a second rod geometry (at 116), as will be described in more detail in relation to FIGS. 3 and 4. The method 100 may include (at 118) displaying, by at least one processor 1105, the first rod geometry and/or the second rod geometry on an image of the spine of the patient, such as a pre-operative image, as shown in FIGS. 9-10.

Figure 9:
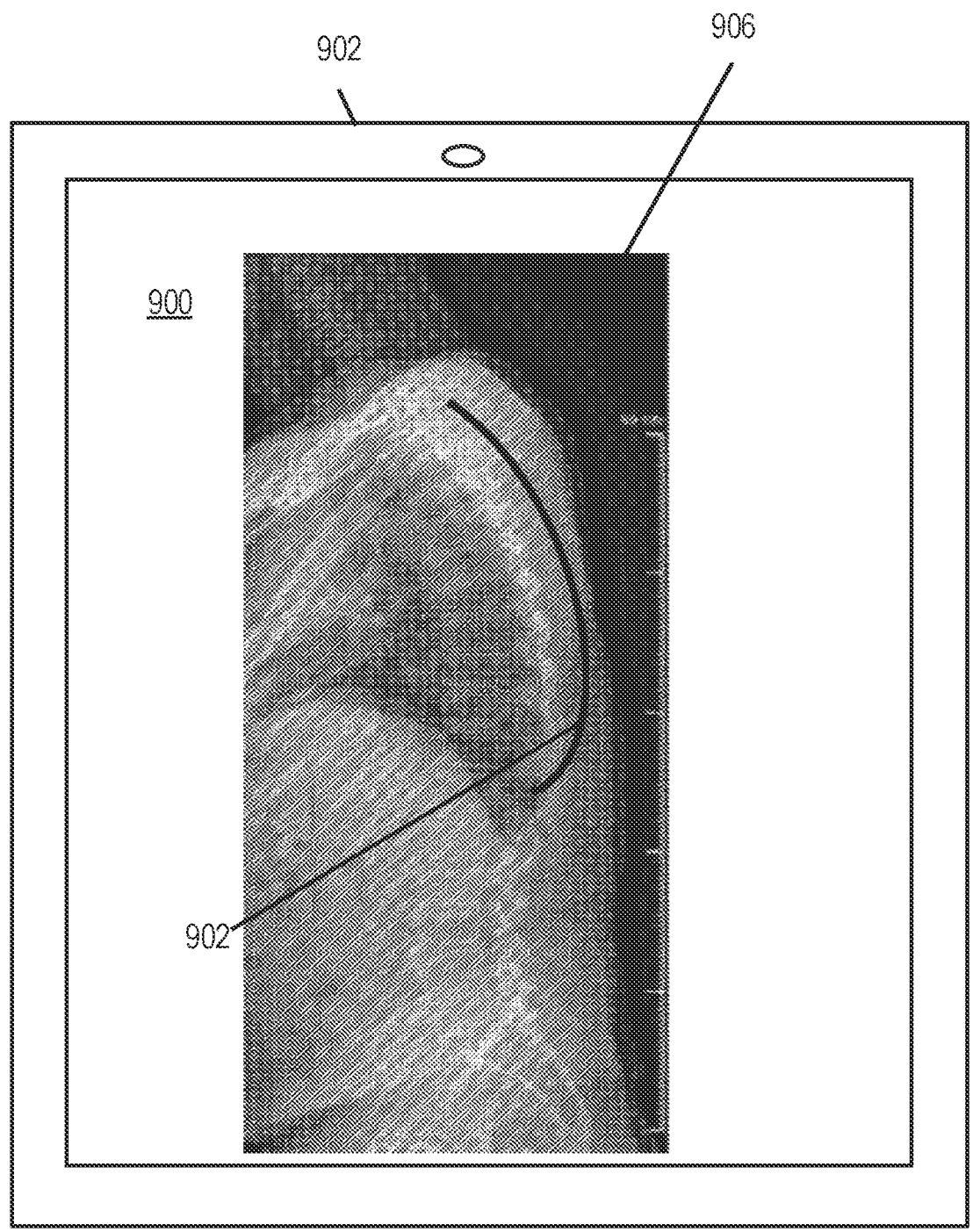
FIG. 9 is an example illustration of a design of a first rod geometry overlaid on a spine in an image of the patient.
Figure 10:
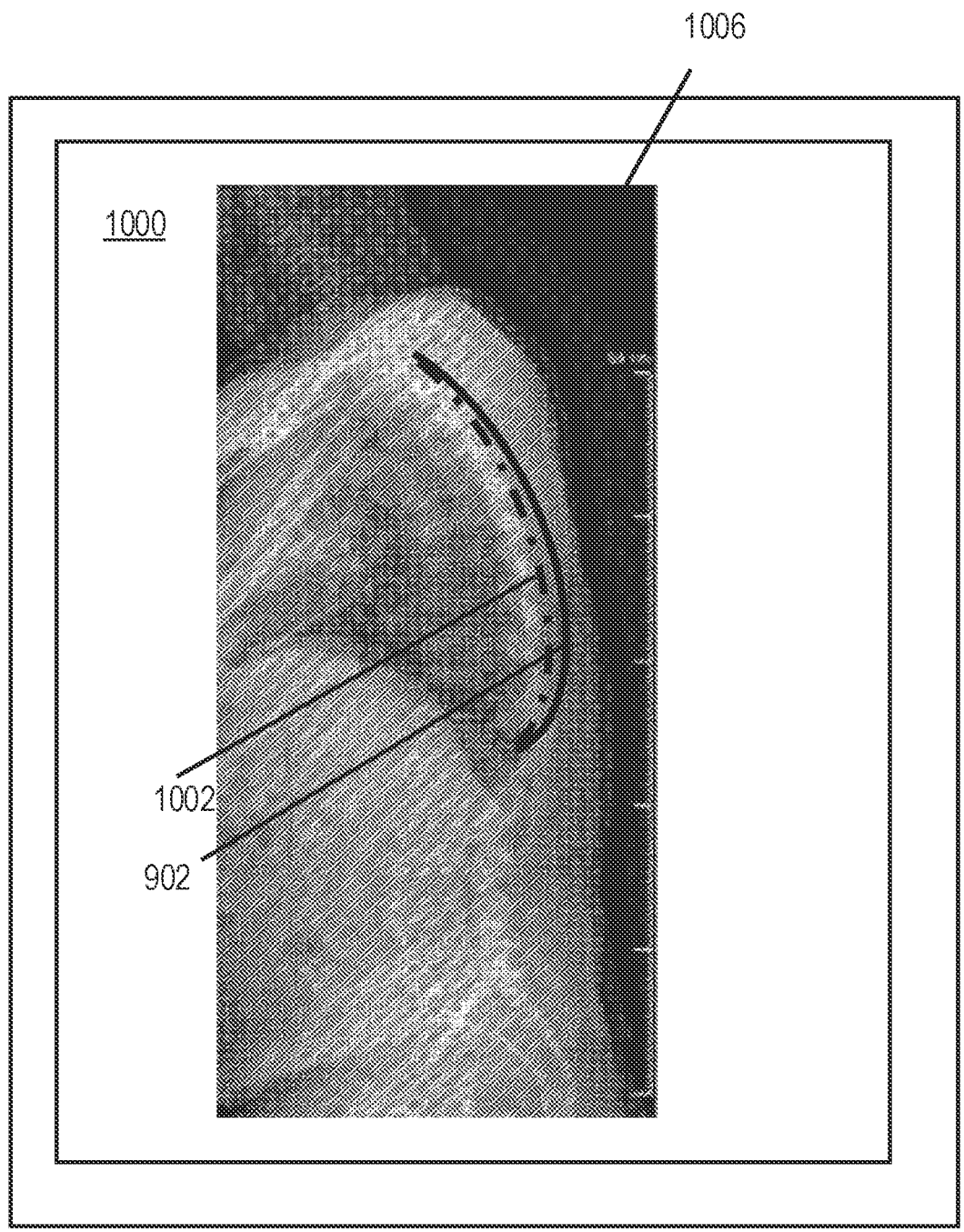
FIG. 10 is an example illustration of designs of first and second rod geometries overlaid on a spine in an image of the patient.

FIG. 9 is an example illustration of a design of a first rod geometry 902 overlaid on a spine in an image 906 of the patient. FIG. 10 is an example illustration of designs of first and second rod geometries 902 and 1002 overlaid on a spine in an image 1006 of the patient. FIG. 9 illustrates a GUI 900 configured to display an image 1006 on a display device 902. The GUI 900 may be configured to output the first rod geometry 902 representative of a first rod, for example, to plan a location for implantation during surgery. In FIG. 10, the GUI 1000 may be configured to output the first rod geometry 902 representative of a first rod and second rod geometry 1002 representative of the second rod, for example, to plan the locations for implantation during surgery.

The method 100 may include (at 116) creating a second rod geometry by performing difference bending of a patient-specific second rod that may be configured to be a compliment to the first rod for the treatment to correct the spine in a patient.

Figure 3:
FIG. 3 is a flowchart that illustrates an example method for designing a patient-specific first rod geometry.
Figure 3:
Figure 3:

FIG. 3 is a flowchart that illustrates an example method 114 for designing a patient-specific first rod geometry. For example, the method 114 may include (at 302), by at least one processor 1105, generating a drawing of a spinal rod having a plurality of spline segments is disclosed in U.S. Ser. No. 17/130,492, entitled "SYSTEMS, METHODS, AND DEVICES FOR DEVELOPING PATIENT-SPECIFIC SPINAL IMPLANTS, TREATMENTS, OPERATIONS, AND/OR PROCEDURES," incorporated herein in its entirety.

The method 114 may include (at 304), by at least one processor 1105, approximating a bend out in a first rod geometry, for example. An example process to determine a bend out of a concave rod is described in "Postoperative Changes in Spinal Rod Contour in Adolescent Idiopathic Scoliosis, An in Vivo Deformation Study," by Krishna R. Cidambi, M D et al., SPINE Vol. 37, No. 18, pp. 1566-1572, copyright 2012, Lippincott Williams & Wilkins, incorporated herein by reference in its entirety. For example, in some embodiments, a overbending or overcontouring by approximately 20° for a concaved rod may provide a minimal amount of loss in sagittal alignment. The bend out to effectuate an increase kyphosis may be determined using machine-learning algorithms 1123 for rod designing 1164 based on trained data between pre-operative and post-operative rod contours, and specifically based on the material used to manufacture the rod. Material properties of biocompatible materials, described above, may each have a deformation signature response to the in vivo deforming forces. The deformation signature response may be a function of the rod length, the rod diameter, the rod material, by way of non-limiting example. The trained data (i.e., datasets 1127) may be determined based on 2D image data, for example, between pre-operative and post-operative rod contours of rods made of varying materials. The process to approximate the bend out of a patient-specific first rod, will be described in more detail in FIG. 4.

The planning of the bend out may also require knowledge of surgery strategies, as determined, for example, by algorithms for surgical strategies 1165 and datasets 1127, based on preferences of the surgeon, actual surgical cases, surgical case simulation or robotic surgery system. For example, bend out may be based on in situ rod bending techniques and/or bending devices. The bend out may be based on instrumentation or processes for rod implantation.

The bending of the rod geometry may be a function of the maximal deflection of the rod with greatest deformation due to bending and an angle of intersection of tangents to the rod end points. The rod geometry generates a first approximation for bending the rod geometry for treatment of the deformity. The second approximation for bending the rod geometry may be an overbending for a concave rod or underbending for a convex rod. The second approximation may be configured to compensate for the deformation signature response of the rod to the in vivo deforming forces.

The method 114 may include (at 306), by at least one processor 1105, performing a difference bending procedure for designing or creating the second rod geometry (at 116).

Figure 4:
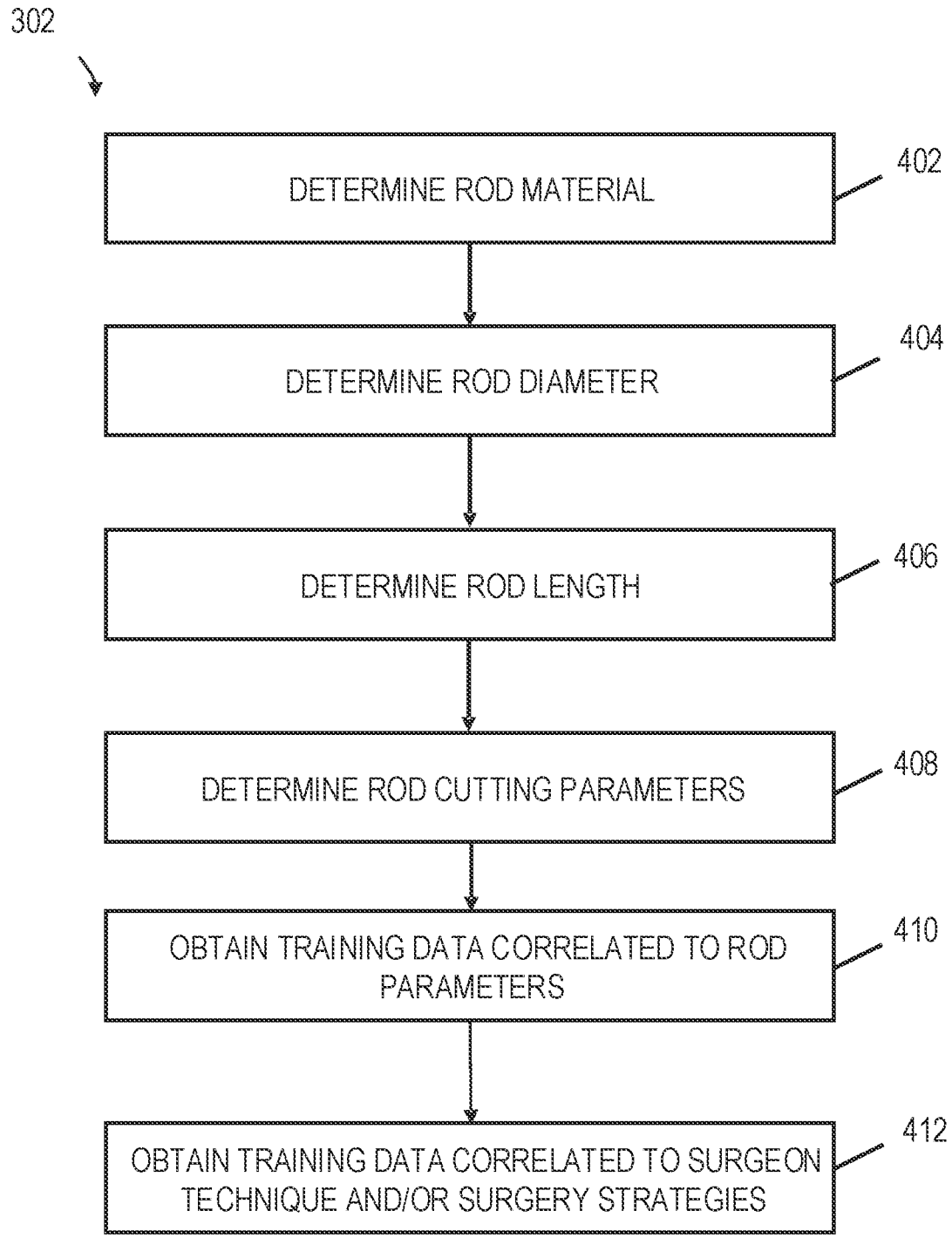
FIG. 4 is a flowchart that illustrates an example method for creating a rod geometry.

FIG. 4 is a flowchart that illustrates an example method 302 for designing a rod geometry. In this example, the rod geometry is for a first rod geometry. The method 302 may include (at 402), by at least one processor 1105, determining rod material and/or (at 404) determining a rod diameter. The method 302 may include (at 406), by at least one processor 1105, determining a rod length and/or (at 408) determining rod cutting parameters. The method 302 may include (at 410) obtaining training data correlated to rod design parameters. The method 302 may include (at 412) obtaining training data from datasets 1127 correlated to surgeon techniques and/or surgery strategies. By way of non-limiting example, the surgeon techniques may include in situ rod bending techniques to cut the final first rod geometry and/or type of bending device to bend a manufactured rod to conform to the final first rod geometry.

The method steps 402, 404, 406 and 408, for example, may be used for developing a deformation signature response of the implanted rod, as certain materials may have a different bending strengths and performance.

The surgery planning system described herein may be part of a navigation processor system 1178 (FIG. 11) may, according to various embodiments include those disclosed in U.S. Pat. Nos. RE44,305; 7,697,972; 8,644,907; and 8,842,893; and U.S. Pat. App. Pub. No. 2004/0199072, all incorporated herein by reference, or may also include the commercially available StealthStation® or Fusion™ surgical navigation systems sold by Medtronic Navigation, Inc. having a place of business in Louisville, Colo.

Before surgery, at least one rod made of biocompatible material may be made to the specification that approximates the at least one rod geometry. The final bent rods may be individually bent by the surgeon using a bending device during surgery. The rods may be bent so that the rods conform to the final rod geometries. Thereafter, using the navigation processor system 1178, the surgeon may proceed to implant each rod according to the planned surgery.

FIG. 11 depicts an example of internal hardware that may be included in any of the electronic components of an electronic device or computing system 1100 as described in this disclosure such as, for example, a computing device, a remote server, cloud computing system, external electronic device and/or any other integrated system and/or hardware that may be used to contain or implement program instructions. The computing system 1100 may be a surgery planning system.

A bus 1110 serves as the main information highway interconnecting the other illustrated components of the hardware. Processor(s) 1105 may be the central processing unit (CPU) of the computing system, performing machine-learning algorithms, calculations and logic operations as may be required to execute a program. CPU 1105, alone or in conjunction with one or more of the other elements disclosed in FIG. 11, is an example of a processor as such term is used within this disclosure. Read only memory (ROM) and random access memory (RAM) constitute examples of tangible and non-transitory computer-readable storage media, memory devices 1120 or data stores as such terms are used within this disclosure. The memory device 1120 may store an operating system (OS) of the computing device, a server or for the platform of the electronic device. The memory device 1120 may include surgery navigation interface 1175 to interface with the (surgery) navigation processor system 1178.

Program instructions 1122, software or interactive modules for providing the interface and performing any querying and analysis. The analysis may include interfacing machine-learning algorithms 1123 be stored in the computer-readable storage media (e.g., memory device 1120). The machine-learning algorithms 1123 includes algorithms for image segmentation 1160, spinal measurements 1161, 2D-to-3D transformation 1163, gap transformation 1163, rod designing 1164, thoracic kyphosis goal module 1166 and surgical strategies 1165 associated with one or more datasets 1127 stored in the computer-readable storage media (e.g., memory device 1120). Optionally, the program instructions may be stored on a tangible, non-transitory computer-readable medium such as a compact disk, a digital disk, flash memory, a memory card, a universal serial bus (USB) drive, an optical disc storage medium and/or other recording medium.

An optional display interface 1130 may permit information from the bus 1110 to be displayed on the display device 1135, such as display device 602, 702, 802, 902 or 1002, in audio, visual, graphic or alphanumeric format. Electronic communication with external devices may occur using various communication ports 1140. A communication port 1140 may be attached to a communications network, such as the Internet or an intranet. In various embodiments, electronic communications with external devices may occur via one or more short range communication protocols. The communication port or devices 1140 may include communication devices for wired or wireless communications and may communicate with a remote server 1190. By way of non-limiting example, the computing system 1100 may receive 2D images 1195 of the patient from a remote server 1190 via communication devices 1140.

The hardware may also include a user interface 1145 that allows for receipt of data from input devices, such as a keyboard or other input device 1150 such as a mouse, a joystick, a touch screen, a remote control, a pointing device, a video input device and/or an audio input device. The GUIs 1170, described herein, may be displayed using a browser application being executed by an electronic device, computing system 1100 and/or served by a remote server (1190). For example, hypertext markup language (HTML) (i.e., programming instructions) may be used for designing the GUI with HTML tags to the images of the patient and other information stored in or served from memory of the server. The GUIs 1170 may include the GUIs 600A, 600B, 700A, 700B, 800, 900 and 1000, for example.

In this document, "electronic communication" refers to the transmission of data via one or more signals between two or more electronic devices, whether through a wired or wireless network, and whether directly or indirectly via one or more intermediary devices. Devices are "communicatively connected" if the devices are able to send and/or receive data via electronic communication.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device or system.

In one or more examples, the described techniques and methods may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that may be used to store desired program code in the form of instructions or data structures and that may be accessed by a computer).

Instructions may be executed by one or more processors 1105, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method, comprising:
by at least one processor:
measuring spinal parameters of a spine in a two-dimensional (2D) pre-operative spinal image including at least a pre-operative thoracic Cobb angle and a pre-operative thoracic kyphosis;
transforming the 2D pre-operative spinal image to a three-dimensional (3D), pre-operative spinal image representation by:
performing segmentation of spine elements in the 2D pre-operative spinal image, and
applying a mathematical formula based on the pre-operative thoracic Cobb angle and the pre-operative thoracic kyphosis to the spine elements;
identifying a thoracic kyphosis goal having a post-operative thoracic kyphosis value to a selected set of the spine elements;
transforming a gap of the spine elements representative of a difference between the pre-operative thoracic kyphosis in the 3D pre-operative spinal image representation and the thoracic kyphosis goal to create a 3D post-operative spinal image representation using a predictive model of gap transformation, the predictive model including machine-learning algorithms trained on medical images of other patients having a thoracic kyphosis; and
determining a first rod design based on the 3D post-operative spinal image representation to achieve the post-operative thoracic kyphosis value in the selected set of spine elements;
determining a deformation signature response of a rod contoured to a geometry of the first rod design based on a material the rod is made of; and
determining a second rod design based on the first rod design, the second rod design configured to compensate for the deformation signature response of the rod.

2. The method of claim 1, further comprising, by the at least one processor:
displaying a graphical user interface including an image representative of the first rod geometry and the second rod geometry relative to the spine.

3. The method of claim 1, further comprising, by the at least one processor:
determining a surgical strategy; and
while determining the surgical strategy, performing at least one of:
determining rod cutting parameters to cut the second rod geometry,
determining in situ rod bending techniques to cut the second rod geometry, or
bending a rod to conform to the second rod geometry.

4. The method of claim 1, wherein identifying the thoracic kyphosis goal having the post-operative thoracic kyphosis value to the selected set of the spine elements comprises selecting the set of spine elements to treat an adolescent idiopathic scoliosis deformity.

5. The method of claim 1, further comprising, by the at least one processor:
segmenting the 2D pre-operative spinal image; and
identifying levels of vertebrae in the segmented 2D pre-operative spinal image,
wherein the measuring of the spinal parameters of the spine is based on the identified levels of the vertebrae.

6. A system, comprising:
at least one processor; and
a non-transitory and tangible computer readable storage medium having programming instructions stored thereon, which when executed are configured to cause the at least one processor to:
  measure spinal parameters of a spine in a two-dimensional (2D) pre-operative spinal image including at least a pre-operative thoracic Cobb angle and a pre-operative thoracic kyphosis;
  transform the 2D pre-operative spinal image to a three-dimensional (3D), pre-operative spinal image representation by:
    performing segmentation of spine elements in the 2D pre-operative spinal image, and
    applying a mathematical formula based on the pre-operative thoracic Cobb angle and the pre-operative thoracic kyphosis to the spine elements;
  identify a thoracic kyphosis goal having a post-operative thoracic kyphosis value to a selected set of the spine elements;
  transform a gap of the spine elements representative of a difference between the pre-operative thoracic kyphosis in the 3D pre-operative spinal image representation and the thoracic kyphosis goal to create a 3D post-operative spinal image representation using a predictive model of gap transformation, the predictive model including machine-learning algorithms trained on medical images of other patients having a thoracic kyphosis;
  determine a first rod design based on the 3D post-operative spinal image representation to achieve the post-operative thoracic kyphosis value in the selected set of spine elements;
  determine a deformation signature response of a rod contoured to a geometry of the first rod design based on a material the rod is made of; and
  determine a second rod design based on the first rod design, the second rod design configured to compensate for the deformation signature response of the rod.

7. The system of claim 6, further comprising programming instructions, which when executed are configured to cause the at least one processor to:
display a graphical user interface comprising:
  an image representative of the first rod geometry and the second rod geometry relative to the spine.

8. The system of claim 6, further comprising programming instructions, which when executed are configured to cause the at least one processor to:
determine a surgical strategy; and
while determining the surgical strategy, perform at least one of:
  determine rod cutting parameters to cut the second rod geometry,
  determine in situ rod bending techniques to cut the second rod geometry, or
  bending a rod to conform to the second rod geometry.

9. The system of claim 6, wherein the selected set of the spine elements are selected to treat an adolescent idiopathic scoliosis deformity.

10. The system of claim 6, further comprising programming instructions, which when executed are configured to cause the at least one processor to:
segment the 2D pre-operative spinal image; and
identify levels of vertebrae in the segmented 2D pre-operative spinal image,
wherein the measuring of the spinal parameters of the spine is based on the identified levels of the vertebrae.

11. A method, comprising:
planning a surgery to correct a spinal deformity according to the method of claim 1;
obtaining a rod formed of biocompatible material configured to approximate the second a first-rod design;
during the surgery, bending the rod to create a bent rod conforming to the second first-rod design; and
implanting the bent rod.

12. The method of claim 11, wherein implanting the bent rod includes affixing the bent rod to a selected set of spine elements,
wherein the selected set of spine elements are selected to treat an adolescent idiopathic scoliosis deformity.

13. The method of claim 1, wherein determining the deformation signature response of the rod comprises determining the deformation signature response based on rod diameter and/or rod length.

14. The method of claim 1, wherein determining the deformation signature response of the rod comprises using a machine-learning algorithm trained on pre-operative and post-operative contours of rods made of the material.

15. The method of claim 14, wherein using the machine-learning algorithm trained on pre-operative and post-operative contours comprises using a machine-learning algorithm trained on 2D image data of pre-operative and post-operative rod contours.

16. The method of claim 1, wherein determining the second rod design comprises configuring the second rod design to compensate for the deformation signature response of the rod due to in vivo deforming forces.

17. The method of claim 16, wherein determining the second rod design comprises configuring the second rod design to compensate for overbending due to in vivo deforming forces.

18. The system of claim 6, wherein the programming instructions that are configured to cause the at least one processor to determine the deformation signature response of the rod comprise programming instructions that are configured to cause the at least one processor to determine the deformation signature response based on rod diameter and/or rod length.

19. The system of claim 6, wherein the programming instructions that are configured to cause the at least one processor to determine the deformation signature response of the rod comprise programming instructions that are configured to cause the at least one processor to use a machine-learning algorithm trained on pre-operative and post-operative contours of rods made of the material.

20. The system of claim 19, wherein the programming instructions that are configured to cause the at least one processor to use the machine-learning algorithm trained on pre-operative and post-operative contours comprises programming instructions that are configured to cause the at least one processor to use a machine-learning algorithm trained on 2D image data of pre-operative and post-operative rod contours.

21. The system of claim 6, wherein the programming instructions that are configured to cause the at least one processor to determine the second rod design comprises programming instructions that are configured to cause the at least one processor to configure the second rod design to compensate for the deformation signature response of the rod due to in vivo deforming forces.

* * * * *